US008119101B2

(12) United States Patent
Byrd et al.

(10) Patent No.: US 8,119,101 B2
(45) Date of Patent: *Feb. 21, 2012

(54) ANTI-CD74 IMMUNOCONJUGATES AND METHODS OF USE

(75) Inventors: John C. Byrd, Columbus, OH (US); David M. Goldenberg, Mendham, NJ (US); Hans J. Hansen, Picayune, MS (US)

(73) Assignees: The Ohio State University, Columbus, OH (US); Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/789,575

(22) Filed: May 28, 2010

(65) Prior Publication Data
US 2010/0272636 A1 Oct. 28, 2010

Related U.S. Application Data

(63) Continuation-in-part of application No. 10/706,852, filed on Nov. 12, 2003, now Pat. No. 7,829,064, which is a continuation-in-part of application No. 10/314,330, filed on Dec. 9, 2002, now Pat. No. 7,837,995, which is a continuation of application No. 09/965,796, filed on Oct. 1, 2001, now Pat. No. 7,910,103, which is a continuation of application No. 09/307,816, filed on May 10, 1999, now Pat. No. 6,306,393, said application No. 10/706,852 is a continuation-in-part of application No. 10/350,096, filed on Jan. 24, 2003, which is a continuation of application No. 09/590,284, filed on Jun. 9, 2000, now Pat. No. 7,074,403, said application No. 10/706,852 is a continuation-in-part of application No. 10/377,122, filed on Mar. 3, 2003, now Pat. No. 7,312,318.

(60) Provisional application No. 61/265,999, filed on Dec. 2, 2009, provisional application No. 60/478,830, filed on Jun. 17, 2003, provisional application No. 60/360,259, filed on Mar. 1, 2002.

(51) Int. Cl.
*A61K 39/44* (2006.01)
*A61K 51/12* (2006.01)
*A61K 9/127* (2006.01)
*A61K 39/00* (2006.01)

(52) U.S. Cl. ............... 424/1.21; 424/178.1; 424/179.1; 424/450; 424/180.1; 424/182.1

(58) Field of Classification Search .................. None
See application file for complete search history.

(56) References Cited

U.S. PATENT DOCUMENTS

| | | |
|---|---|---|
| 4,036,945 A | 7/1977 | Haber |
| 4,046,722 A | 9/1977 | Rowland |
| 4,331,647 A | 5/1982 | Goldenberg |
| 4,699,784 A | 10/1987 | Shih et al. |
| 4,704,692 A | 11/1987 | Ladner |
| 4,816,567 A | 3/1989 | Cabilly et al. |
| 4,824,659 A | 4/1989 | Hawthorne |
| 4,916,213 A | 4/1990 | Scannon et al. |
| 4,918,163 A | 4/1990 | Young et al. |
| 4,925,922 A | 5/1990 | Byers et al. |
| 4,932,412 A | 6/1990 | Goldenberg |
| 4,946,778 A | 8/1990 | Ladner et al. |
| 5,057,313 A | 10/1991 | Shih et al. |
| 5,106,955 A | 4/1992 | Endo et al. |
| 5,134,075 A | 7/1992 | Hellstrom et al. |
| 5,171,665 A | 12/1992 | Hellstrom et al. |
| 5,196,337 A | 3/1993 | Ochi et al. |
| 5,204,095 A | 4/1993 | Goodall et al. |
| 5,229,275 A | 7/1993 | Goroff |
| 5,443,953 A | 8/1995 | Hansen et al. |
| 5,484,892 A | 1/1996 | Tedder et al. |
| 5,525,338 A | 6/1996 | Goldenberg |
| 5,565,215 A | 10/1996 | Gref et al. |
| 5,567,610 A | 10/1996 | Borrebaeck et al. |
| 5,593,676 A | 1/1997 | Bhat et al. |
| 5,618,920 A | 4/1997 | Robinson et al. |
| 5,620,708 A | 4/1997 | Amkraut et al. |
| 5,633,425 A | 5/1997 | Lonberg et al. |

(Continued)

FOREIGN PATENT DOCUMENTS
EP 0332865 9/1989
(Continued)

OTHER PUBLICATIONS
Hertlein et al. (Blood, 2010, 116: 2554-2558).*
(Continued)

*Primary Examiner* — Peter J Reddig
*Assistant Examiner* — Yan Xiao
(74) *Attorney, Agent, or Firm* — Richard A. Nakashima

(57) ABSTRACT

Disclosed are compositions that include anti-CD74 immunoconjugates and optionally a therapeutic and/or diagnostic agent. In preferred embodiments, the immunoconjugates comprise one or more anti-CD74 antibodies or antigen-binding fragments thereof, conjugated to a liposome or micelle. Also disclosed are methods for preparing the immunoconjugates and using the immunoconjugates in diagnostic and therapeutic procedures. In certain preferred embodiments, the therapeutic methods comprise administering to a subject with a CD74-expressing disease an anti-CD74 immunoconjugate and thereby inducing apoptosis of CD74-expressing cells. In more preferred embodiments, the CD74 immunoconjugate is capable of inducing cell death in the absence of any other therapeutic agent, although such agents may be optionally administered prior to, together with or subsequent to administration of the anti-CD74 immunoconjugate. The compositions may be part of a kit for administering the anti-CD74 immunoconjugates or compositions.

34 Claims, 11 Drawing Sheets

U.S. PATENT DOCUMENTS

| | | | |
|---|---|---|---|
| 5,686,072 | A | 11/1997 | Uhr et al. |
| 5,693,762 | A | 12/1997 | Queen et al. |
| 5,698,178 | A | 12/1997 | Goldenberg |
| 5,702,727 | A | 12/1997 | Amkraut et al. |
| 5,716,595 | A | 2/1998 | Goldenberg |
| 5,736,119 | A | 4/1998 | Goldenberg et al. |
| 5,776,456 | A | 7/1998 | Anderson et al. |
| 5,789,554 | A | 8/1998 | Leung et al. |
| 5,792,845 | A | 8/1998 | O'Reilly et al. |
| 5,795,967 | A | 8/1998 | Aggarwal et al. |
| 5,798,554 | A | 8/1998 | Grimaldi et al. |
| 5,874,540 | A | 2/1999 | Hansen et al. |
| 5,922,302 | A | 7/1999 | Goldenberg et al. |
| 6,051,228 | A | 4/2000 | Aruffo et al. |
| 6,051,230 | A | 4/2000 | Thorpe et al. |
| 6,077,499 | A | 6/2000 | Griffiths et al. |
| 6,096,289 | A | 8/2000 | Goldenberg |
| 6,165,440 | A | 12/2000 | Esenaliev |
| 6,183,744 | B1 | 2/2001 | Goldenberg |
| 6,187,287 | B1 | 2/2001 | Leung et al. |
| 6,254,868 | B1 | 7/2001 | Leung et al. |
| 6,306,393 | B1 | 10/2001 | Goldenberg |
| 6,331,175 | B1 | 12/2001 | Goldenberg |
| 6,379,698 | B1 | 4/2002 | Leamon |
| 6,387,350 | B2 | 5/2002 | Goldenberg |
| 6,395,276 | B1 | 5/2002 | Rybak et al. |
| 6,530,944 | B2 | 3/2003 | West et al. |
| 6,562,318 | B1 | 5/2003 | Filler |
| 6,653,104 | B2 | 11/2003 | Goldenberg |
| 7,074,403 | B1 | 7/2006 | Goldenberg et al. |
| 7,387,779 | B2 | 6/2008 | Kalluri |
| 7,829,064 | B2 * | 11/2010 | Griffiths et al. ............ 424/1.21 |
| 2002/0018749 | A1 | 2/2002 | Hudson et al. |
| 2004/0076683 | A1 | 4/2004 | Hoarau et al. |
| 2004/0197328 | A1 * | 10/2004 | Young et al. ............... 424/141.1 |
| 2010/0266496 | A1 * | 10/2010 | Hansen et al. ............... 424/1.49 |
| 2011/0070155 | A1 * | 3/2011 | Griffiths et al. ............ 424/1.21 |

FOREIGN PATENT DOCUMENTS

| | | |
|---|---|---|
| EP | 0510949 | 10/1992 |
| WO | 91/13974 | 9/1991 |
| WO | 94/27638 | 12/1994 |
| WO | 9509917 | 4/1995 |
| WO | 96/04925 | 2/1996 |
| WO | 98/42378 | 10/1998 |
| WO | 98/50435 | 11/1998 |
| WO | 99/02567 | 1/1999 |
| WO | 99/54440 | 10/1999 |
| WO | 00/29584 | 5/2000 |
| WO | 00/67795 | 11/2000 |
| WO | 00/74718 | 12/2000 |

OTHER PUBLICATIONS

Dillman (Annals of Internal Medicine, 1989 111:592-603).*

Press et al., "Prospects for the management of non-Hodgkin's lymphomas with monoclonal antibodies and immunoconjugates", Cancer J. Sci. Am. 4(Suppl 2):S19-26 (1998).

Price, K. M., "Production and characterization of synthetic peptide-derived antibodies", Monoclonal Antibodies: Production, Engineering and Clinical Application, Ritter et al., (Eds.), pp. 60-84, Cambridge University Press (1995).

Protheroe et al., "Remission of inflammatory arthropathy in association with anti-CD20 therapy for non-Hodgkin's lymphoma", Rheumatology (Oxford) 38(11):1150-2 (1999).

Qu et al., "Carbohydrates engineered at antibody constant domains can be used for site-specific conjugation of drugs and chelates", J. Immunol. Methods 213(2):131-44 (1998).

Qu et al., "Internalization and cytotoxic effects of a humanized anti-CD74 antibody, LL1", Proc Am Assoc Cancer Res 2002;43:255, Abstract # 1269.

Raag et al., "Single-chain Fvs", FASEB J. 9(1):73-80 (1995).

Renner et al., "Monoclonal antibodies in the treatment of non-Hodgkin's lymphoma: recent results and future prospects", Leukemia 11(Suppl 2):S55-9 (1997).

Riechmann et al., "Reshaping human antibodies for therapy", Nature 332(6162):323-7 (1988).

Rowan et al., "Cross-linking of the CAMPATH-1 antigen (CD52) mediates growth inhibition in human B- and T-lymphoma cell lines, and subsequent emergence of CD52-deficient cells", Immunology 95(3):427-36 (1998).

Rudikoff et al., "Single amino acid substitution altering antigen-binding specificity", Proc. Natl. Acad. Sci. USA 79 (6):1979-83 (1982).

Ryser et al., "Conjugation of methotrexate to poly(L-lysine) increases drug transport and overcomes drug resistance in cultured cells", Proc. Natl. Acad. Sci. USA 75(8):3867-70 (1978).

Saltzman et al., "Transport rates of proteins in porous materials with known microgeometry", Biophys. J. 55 (1):163-71 (1989).

Sandhu, J. S., "Protein engineering of antibodies", Crit. Rev. Biotechnol. 12(5-6):437-62 (1992).

Schlom, J. "Monoclonal Antibodies: They're More and Less Than You Think", Molecular Foundations of Oncology, Broader, S. (Ed.), pp. 95-134 (1991).

Sherwood et al., "Controlled antibody delivery systems", Biotechnology 10(11):1446-9 (1992).

Shih et al., "Site-specific linkage of methotrexate to monoclonal antibodies using an intermediate carrier", Int J Cancer 41(6):832-9 (1988).

Shih et al., "A fluorouridine-anti-CEA immunoconjugate is therapeutically effective in a human colonic cancer xenograft model", Int. J. Cancer 46(6):1101-6 (1990).

Shih et al., "Internalization and intracellular processing of an anti-B-cell lymphoma monoclonal antibody, LL2", Int J Cancer 56(4):538-45 (1994).

Shih et al., "Localization of an antibody to CD74 (MHC class II invariant chain) to human B cell lymphoma xenografts in nude mice", Cancer Immunol. Immunother. 49(4-5):208-16 (2000).

Singer et al., "Optimal humanization of 1B4, an anti-CD18 murine monoclonal antibody, is achieved by correct choice of human V-region framework sequences", J. Immunol. 150(7):2844-57 (1993).

Stein et al., "Epitope specificity of the anti-(B cell lymphoma) monoclonal antibody, LL2", Cancer Immunol. Immunother. 37(5):293-8 (1993).

Straubinger et al., "Endocytosis and intracellular fate of liposomes using pyranine as a probe", Biochemistry 29 (20):4929-39 (1990).

Tatsuta et al., "Diagnosis of gastric cancers with fluorescein-labeled monoclonal antibodies to carcinoembryonic antigen", Lasers Surg. Med. 9(4):422-6 (1989).

Taylor et al., "A transgenic mouse that expresses a diversity of human sequence heavy and light chain immunoglobulins", Nucleic Acids Res. 20(23):6287-95 (1992).

Tempest et al., "Reshaping a human monoclonal antibody to inhibit human respiratory syncytial virus infection in vivo", Biotechnology 9(3):266-71 (1991).

Theocharis et al., "Characterization of in vivo mutated T cell clones from patients with systemic lupus erythematosus", Clin. Immunol. Immunopathol. 74(2):135-42 (1995).

Thorpe et al., "Monoclonal antibodies: clinical and regulatory issues", Trends Biotechnol. 11(2):40-2 (1993).

Torchilin et al., "The antibody-linked chelating polymers for nuclear therapy and diagnostics", Crit. Rev. Ther. Drug Carrier Syst. 7(4):275-308 (1991).

Torchilin et al., "Immunomicelles: targeted pharmaceutical carriers for poorly soluble drugs", Proc. Natl. Acad. Sci. USA 100(10):6039-44 (2003).

Upeslacis et al., "Modification of Antibodies by Chemical Methods," Monoclonal Antibodies: Principles and Applications, Birch et al. (eds.), pp. 187-230 (Wiley-Liss, Inc., 1995).

Van Den Bergh, H., "Light and porphyrins in cancer therapy", Chem. Britain 22:430 (1986).

Vaughan et al., "Human antibodies with sub-nanomolar affinities isolated from a large non-immunized phage display library", Nat. Biotechnol. 14(3):309-14 (1996).

Verhoeyen et al., "Reshaping human antibodies: grafting an antilysozyme activity", Science 239(4847):1534-6 (1988).

Vuist et al., "Potentiation by interleukin 2 of Burkitt's lymphoma therapy with anti-pan B (anti-CD19) monoclonal antibodies in a mouse xenotransplantation model", Cancer Res. 49(14):3783-8 (1989).

Ward et al., "Genetic Manipulation and Expression of Antibodies," Monoclonal Antibodies: Principles and Applications, Birch et al., (eds.), pp. 137-185 (Wiley-Liss, Inc. 1995).

West et al., "Applications of nanotechnology to biotechnology commentary", Curr Opin Biotechnol. 11(2):215-7 (2000).

Wong, S. Chemistry of Protein Conjugation and Cross-Linking, CRC Press, Inc. (1991).

Wrobel et al., "Fusion of cationic liposomes with mammalian cells occurs after endocytosis", Biochim. Biophys. Acta. 1235(2):296-304 (1995).

Xu et al., "Systemic tumor-targeted gene delivery by anti-transferrin receptor scFv-immunoliposomes", Mol. Cancer Ther. 1(5):337-46 (2002).

Yu et al., "Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells", Int. J. Cancer 56(2):244-8 (1994).

Koning et al., "Selective transfer of a lipophilic prodrug of 5-fluorodeoxyuridine from immunoliposomes to colon cancer cells", Biochim. Biophys. Acta. 1420(1-2):153-67 (1999).

Kratz et al., "Drug-polymer conjugates containing acid-cleavable bonds", Crit. Rev. Ther. Drug Carrier Syst. 16(3):245-88 (1999).

Kreitman et al., "*Pseudomonas* exotoxin-based immunotoxins containing the antibody LL2 or LL2-Fab' induce regression of subcutaneous human B-cell lymphoma in mice", Cancer Res. 53(4):819-25 (1993).

Larrick et al., "PCR Amplification of Antibody Genes", Methods: A Companion to methods in Enzymology 2 (2):106-110 (1991).

Lazar et al.,"Transforming growth factor alpha: mutation of aspartic acid 47 and leucine 48 results in different biological activities", Mol. Cell. Biol. 8(3):1247-1252 (1988).

Leonard et al., "Epratuzumab, a new Anti-CD22, humanized, monoclonal antibody for the therapy of non-Hodgkin's lymphoma (NHL): phase I/II trial results", Blood 94:92a-93a, Abstract # 404, (1999).

Leung et al., "Chimerization of LL2, a Rapidly Internalizing Antibody Specific for B Cell Lymphoma", Hybridoma 13 (6):469-476 (1994).

Leung et al., "Engineering a Unique Glycosylation Site for Site-Specific Conjugation of Haptens to Antibody Fragments", J. Immunol. 154:5919-5926 (1995).

Leung et al., "Construction and characterization of a humanized, internalizing, b-cell (CD22)-specific, leukemia/lymphma antibody, LL2", Mol. Immunol. 32(17/18):1413-1427 (1995).

Levine et al., "IgM antibody-related polyneuropathies: B-cell depletion chemotherapy using Rituximab", Neurology 52 (8):1701-4 (1999).

Li et al., "The epitope specificity and tissue reactivity of four murine monoclonal anti-CD22 antibodies", Cell Immunol. 118(1):85-99 (1989).

Lonberg et al., "Antigen-specific human antibodies from mice comprising four distinct genetic modifications", Nature 368:856-9 (1994).

Longo, D. L. "Immunotherapy for non-Hodgkin's lymphoma", Curr. Opin. Oncol. 8(5):353-9 (1996).

Lopez De Menezes et al., "In vitro and in vivo targeting of immunoliposomal doxorubicin to human B-cell lymphoma", Cancer Res. 58(15):3320-30 (1998).

Lopez De Menezes et al., "Cellular Trafficking and Cytotoxicity of Anti-Cd19-Targeted Liposomal Doxorubicin in B Lymphoma Cells", J. Liposome Research 1999, vol. 9, No. 2 , pp. 199-228.

Lundberg, B. "Preparation of drug-carrier emulsions stabilized with phosphatidylcholine-surfactant mixtures", J. Pharm. Sci. 83(1):72-5 (1994).

Lundberg, B. "The solubilization of lipophilic derivatives of podophyllotoxins in sub-micron sized lipid emulsions and their cytotoxic activity against cancer cells in culture", Int. J. Pharm. 109:73-81 (1994).

Lundberg et al., "Submicron lipid emulsions containing amphipathic polyethylene glycol for use as drug-carriers with prolonged circulation time", Int. J. Pharm. 134:119-127 (1996).

Lundberg et al., A submicron lipid emulsion coated with amphipathic polyethylene glycol for parenteral administration of paclitaxel (Taxol), J Pharm Pharmacol. 49:16-21 (1997).

Lundberg et al., "Biologically active camptothecin derivatives for incorporation into liposome bilayers and lipid emulsions", Anticancer Drug Des. 13(5):453-61 (1998).

Lundberg et al., "Conjugation of an anti-B-cell lymphoma monoclonal antibody, LL2, to long-circulating drug-carrier lipid emulsions", J. Pharm. Pharmacol. 51(10):1099-105 (1999).

Lundberg et al., "Specific binding of sterically stabilized anti-B-cell immunoliposomes and cytotoxicity of entrapped doxorubicin", Int. J. Pharm. 205(1-2):101-8 (2000).

Lundberg et al., "Cellular association and cytotoxicity of anti-CD74-targeted lipid drug-carriers in B lymphoma cells", J. Control. Release 94(1):155-61 (2004).

Mack et al., "A small bispecific antibody construct expressed as a functional single-chain molecule with high tumor cell cytotoxicity", Proc. Natl. Acad. Sci. USA 92:7021-7025 (1995).

Maloney et al., "Phase I clinical trial using escalating single-dose infusion of chimeric anti-CD20 monoclonal antibody (IDEC-C2B8) in patients with recurrent B-cell lymphoma", Blood 84(8):2457-66 (1994).

Maranhao et al., "Association of carmustine with a lipid emulsion: in vitro, in vivo and preliminary studies in cancer patients", Cancer Chemother. Pharmacol. 49(6):487-98 (2002).

McCafferty et al., "Phage antibodies: filamentous phage displaying antibody variable domains", Nature 348:552-553 (1990).

Mendez et al., "Functional transplant of megabase human immunoglobulin loci recapitulates human antibody response in mice", Nature Genetics 15:146-156 (1997).

Mew et al., "Photoimmunotherapy: treatment of animal tumors with tumor-specific monoclonal antibody-hematoporphyrin conjugates", J. Immunol. 130(3):1473-7 (1983).

Mew et al., "Ability of Specific Monoclonal Antibodies and Conventional Antisera Conjugated to Hematoporphyrin to Label and Kill Selected Cell Lines Subsequent to Light Activation", Cancer Res. 45:4380-4386 (1985).

Moase et al., "Anti-MUC-1 immunoliposomal doxorubicin in the treatment of murine models of metastatic breast cancer", Biochim. Biophys. Acta. 1510(1-2):43-55 (2001).

Moller et al., "CD74", J. Biol. Regul. Homeost. Agents 14(4):299-301 (2000).

Mosmann, T., "Rapid colorimetric assay for cellular growth and survival: application to proliferation and cytotoxicity assays", J. Immunol. Methods 65(1-2):55-63 (1983).

Nagel et al., "HLXB9 activates IL6 in Hodgkin lymphoma cell lines and is regulated by PI3K signalling involving E2F3", Leukemia 19(5):841-6 (2005).

Nakagawa et al., "Clinical trial of intrathecal administration of 5-fluoro-2'-deoxyuridine for treatment of meningeal dissemination of malignant tumors", J. Neurooncol. 45(2):175-83 (1999).

Nisonoff et al., "Separation of Univalent Fragments from the Bivalent Rabbit Antibody Molecule by Reduction of Disulfide Bonds", Arch. Biochem. Biophys. 89:230-244 (1960).

Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Cancer Res. 7(6):1505-1510 (2001).

Orlandi et al., "Cloning immunoglobulin variable domains for expression by the polymerase chain reaction", Proc. Natl. Acad. Sci. USA 86:3833-3837 (1989).

Oseroff et al., "Antibody-targeted photolysis: Selective photodestruction of human T-cell leukemia cells using monoclonal antibody-chlorin e6 conjugates", Proc. Natl. Acad. Sci. USA 83:8744-8748 (1986).

Oseroff et al., "Strategies for selective cancer photochemotherapy: antibody-targeted and selective carcinoma cell photolysis", Photochem. Potobiol. 46(1):83-96 (1987).

Oster et al., "Erythropoietin for the Treatment of Anemia of Malignancy Associated with Neoplastic Bone Marrow Infiltration", J. Clin. Oncol. 8(6):956-962 (1990).
Pastan et al., "Immunotoxins", Cell 47:641-648 (1986).
Patti et al., "High-dose cyclophosphamide, etoposide and BCNU (CVB) with autologous stem cell rescue in malignant lymphomas", Eur. J. Haematol. 51(1):18-24 (1993).
Pawlak-Byczkowska et al., "Two new monoclonal antibodies, EPB-1 and EPB-2, reactive with human lymphoma", Cancer Res. 49(16):4568-77 (1989).
Pelegrin et al., "Antibody-Fluorescein Conjugates for Photoimmunodiagnosis of Human Colon Carcinoma in Nude Mice", Cancer 67:2529-2537 (1991).
Perkins et al., "Novel therapeutic nano-particles (lipocores): trapping poorly water soluble compounds", Int. J. Pharm. 200(1):27-39 (2000).
Pirker et al., "Characterization of immunotoxins active against ovarian cancer cell lines", J. Clin. Invest. 76(3):1261-7 (1985).
Porter et al., "The Hydrolysis of Rabbit γ-Globulin and Antibodies with Crystalline Papain", Biochem. J. 73 (1):119-127 (1959).
Press et al., "Radiolabeled-antibody therapy of B-cell lymphoma with autologous bone marrow support", N. Engl. J. Med. 329(17):1219-24 (1993).
Press et al., "Phase II trial of 131I-B1 (anti-CD20) antibody therapy with autologous stem cell transplantation for relapsed B cell lymphomas", Lancet 346:336-40 (1995).
Bagshawe et al., "Developments with targeted enzymes in cancer therapy", Curr. Opin. Immunol. 11(5):579-83 (1999).
Bally et al. (Eds.), "Controlling the Drug Delivery Attributes of Lipid-Based Drug Formulations", Journal of Liposome Research, 1998, vol. 8, No. 3, pp. 299-335.
Beers et al., The Merck Manual of Diagnosis and Therapy, Ch. 180, p. 1474-1476; 17th Ed., Whitehouse Station, NJ, Merck Research Labs (1999).
Bendas et al., "Immunoliposomes: a promising approach to targeting cancer therapy", BioDrugs 15(4):215-24 (2001).
Bendig, M., "Humanization of Rodent Monoclonal Antibodies by CDR Grafting", Academic Press Inc., New York, NY, vol. 8, (1995), pp. 83-93.
Bird et al., "Single chain antibody variable regions", Trends Biotechnol. 9(4):132-7 (1991).
Bom et al., "The highly lipophilic DNA topoisomerase I inhibitor DB-67 displays elevated lactone levels in human blood and potent anticancer activity", J. Control Release 74(1-3):325-33 (2001).
Breen et al., "Non-Hodgkin's B cell lymphoma in persons with acquired immunodeficiency syndrome is associated with increased serum levels of IL10, or the IL10 promoter -592 C/C genotype", Clin. Immunol. 109(2):119-29 (2003).
Burgess et al., "Possible dissociation of the heparin-binding and mitogenic activities of heparin-binding (acidic fibroblast) growth factor-1 from its receptor-binding activities by site-directed mutagenesis of a single lysine residue", J. Cell Biol. 111:2129-2138 (1990).
Carter et al., "Humanization of an anti-p185HER2 antibody for human cancer therapy", Proc. Natl. Acad. Sci. USA 89(10):4285-9 (1992).
Chen et al., "Differential Effects of Milatuzumab on Human Antigen-Presenting Cells in Comparison to Malignant B Cells", 2009 ASH Annual Meeting Abstracts, vol. 114(22)1073; Abstr # 2744 (Nov. 20, 2009).
Cochlovius et al., "Cure of Burkitt's lymphoma in severe combined immunodeficiency mice by T cells, tetravalent CD3 × CD19 tandem diabody, and CD28 costimulation", Cancer Res. 60(16):4336-41 (2000).
Coligan et al., (Eds.), Current Protocols in Immunology, vol. 1, pp. 2.5.1-2.6.7; pp. 2.7.1.-2.7.12; pp. 2.8.1-2.8.10; pp. 2.9.1-2.9.3; pp. 2.10.-2.10.4; John Wiley & Sons, Inc., 1991.
Colman, P., "Effects of amino acid sequence changes on antibody-antigen interactions", Res. Immunol. 1994, 145:33-36.
Coloma et al., "Design and production of novel tetravalent bispecific antibodies", Nat. Biotechnol. 15(2):159-63 (1997).
Constantinides et al., "Formulation development and antitumor activity of a filter-sterilizable emulsion of paclitaxel", Pharm. Res. 17(2):175-82 (2000).
Courtenay-Luck, N. S., "Genetic manipulation of monoclonal antibodies", Monoclonal Antibodies: Production, Engineering and Clinical Application, p. 166-179, Ritter et al. (Eds.), Cambridge University Press (1995).
Fitzgerald et al., "Improved tumour targeting by disulphide stabilized diabodies expressed in *Pichia pastoris*", Protein Eng. 10(10):1221-5 (1997).
Flavell et al., "Systemic therapy with 3BIT, a triple combination cocktail of anti-CD19, -CD22, and -CD38-saporin immunotoxins, is curative of human B-cell lymphoma in severe combined immunodeficient mice", Cancer Res. 57:4824-9 (1997).
Freedman et al., "Non-Hodgkin's Lymphomas", Cancer Medicine, 3rd Ed., vol. 2, p. 2028-2068, Holland et al., (Eds.), Lea & Febiger (1993).
French et al., "Response of B-cell lymphoma to a combination of bispecific antibodies and saporin", Leuk. Res. 20 (7):607-17 (1996).
Ghetie et al., "Evaluation of ricin A chain-containing immunotoxins directed against CD19 and CD22 antigens on normal and malignant human B-cells as potential reagents for in vivo therapy", Cancer Res. 48(9):2610-7 (1988).
Gold et al., "Expression of CD74 in pancreatic and colorectal carcinomas as a basis for milatuzumab immunotherapy", Abstract #5485; Proceeding of the American Association for Cancer Research, vol. 50, p. 1322-1323; Apr. 2009.
Goldenberg, D. M. "Radiolabeled antibodies", Science & Medicine, 1(1):64 (Apr. 1994).
Goldenberg, D. M. "Future role of radiolabeled monoclonal antibodies in oncological diagnosis and therapy", Semin. Nucl. Med. 19(4):332-9 (1989).
Goldenberg, D. M. "New Developments in Monoclonal Antibodies for Cancer Detection and Therapy", CA Cancer J. Clin. 44(1):43-64 (1994).
Gondo et al., "HLA class II antigen associated invariant chain gene expression in malignant lymphoma", Br. J. Haematol. 67(4):413-7 (1987).
Goto et al. "A novel membrane antigen selectively expressed on terminally differentiated human B cells", Blood 84 (6):1922-30 (1994).
Green et al., "Antigen-specific human monoclonal antibodies from mice engineered with human Ig heavy and light chain YACs", Nature Genetics 7:13-21 (1994).
Greenwood et al., "Effector functions of matched sets of recombinant human IgG subclass antibodies", Protein Engineering of Antibody Molecules for Prophylactic and Therapeutic Applications in Man, Clark (Ed.), p. 89; p. 97; Academic Titles (1993).
Griffiths et al., "Cure of SCID Mice Bearing Human B-Lymphoma Xenografts by an Anti-CD74 Antibody-Anthracycline Drug Conjugate", vol. 9, 6567-6571, Dec. 15, 2003.
Hansen et al., "Internalization and catabolism of radiolabelled antibodies to the MHC class-II invariant chain by B-cell lymphomas", Biochem. J. 1996, 320:293-300.
Hasan et al., "Laser-induced selective cytotoxicity using monoclonal antibody-chromophore conjugates", Prog. Clin. Biol. Res. 288:471-7 (1989).
Hekman et al. "Initial experience with treatment of human B cell lymphoma with anti-CD19 monoclonal antibody", Cancer Immunol. Immunother. 1991;32(6):364-72.
Hertlein et al., "Immunoliposomes Incorporated with Humanized Monoclonal Antibody, Milatuzumab, Induce Cell Death in CLL by Retention of the CD74 Receptor on the Surface of B Cells" 2009 ASH Annual Meeting Abstracts, vol. 114(22):301; Abstr # 721 (Nov. 20, 2009).
Hertlein et al. "Milatuzumab immunoliposomes induce cell death in CLL by promoting accumulation of CD74 on the surface of B cells", Blood. Jun. 23, 2010. [Epub ahead of print].
Hess et al., "Specificity of effector T lymphocytes in autologous graft-versus-host disease: role of the major histocompatibility complex class II invariant chain peptide", Blood 89(6):2203-9 (1997).

Hong et al., "pH-sensitive, serum-stable and long-circulating liposomes as a new drug delivery system", J. Pharm. Pharmacol. 54(1):51-8 (2002).

Hua et al., "Immunoreactivity for LN2 and LN3 distinguishes small cell carcinomas from non-small cell carcinomas in the lung", Hum. Pathol. 29(12):1441-6 (1998).

Huse et al., "Generation of a Large Combinatorial Library of the Immunoglobulin Repertoire in Phage Lambda", Science 246:1275-1281 (1989).

Ibragimova et al., "Stability of the beta-sheet of the WW domain: A molecular dynamics simulation study", Biophys. J. 77(4):2191-8 (1999).

Johnson et al., "Human antibody engineering", Current Opin. Struct. Biol. 3:564-571 (1993).

Jones et al., "Replacing the complementarity-determining regions in a human antibody with those from a mouse" Nature 321(6069):522-5 (1986).

Juweid et al., "99Tcm-LL1: a potential new bone marrow imaging agent", Nucl. Med. Commun. 18(2):142-8 (1997).

Juweid et al., "Treatment of non-Hodgkin's lymphoma with radiolabeled murine, chimeric, or humanized LL2, an anti-CD22 monoclonal antibody", Cancer Res. 55(23 Suppl):5899s-5907s (1995).

Kaminski et al., "Radioimmunotherapy of B-cell lymphoma with [131I]anti-B1 (anti-CD20) antibody", N. Engl. J. Med. 329(7):459-65 (1993).

Kiesel et al., "Removal of cells from a malignant B-cell line from bone marrow with immunomagnetic beads and with complement and immunoglobulin switch variant mediated cytolysis", Leuk. Res. 11(12):1119-25 (1987).

Kirpotin et al., "Sterically stabilized anti-HER2 immunoliposomes: design and targeting to human breast cancer cells in vitro", Biochemistry 36(1):66-75 (1997).

Kohler et al., "Continuous cultures of fused cells secreting antibody of predefined specificity", Nature 256:495-7 (1975).

Kolata, G., "Clinical promise with new hormones", Science 236:517-519 (1987).

US 6,558,648, 05/2003, Griffiths et al. (withdrawn)

* cited by examiner

LL1VH

```
       CAGATCCAGTTGGTGCAGTCTGGACCTGAGCTGAAGAAGCCTGGAGAGACAGTCAAGTCACCTGCAAGACTTCTCTGATATACCTTCACA
       ----+----|----+----|----+----|----+----|----+----|----+----|----+----|----+----|----+----|    90
       GTCTAGGTCAACCACGTCAGACCTGGACTCGACTTCTTCGGACCTCTCTGTCAGTTGGACCTGCAAGAGACTCTATGGAAGTGT
         Q  I  Q  L  V  Q  S  G  P  E  L  K  K  P  G  E  T  V  K  T  C  K  T  S  G  Y  T  F  T
                                  10                  20                  30

AACTATGGAGTGAACTGGATAAAGCAGACTCCAGGAGAGGGTTTACAGTGGATGGGCTGGATAAACCCCAACACTGGAGAGCCAACATTT
       ----+----|----+----|----+----|----+----|----+----|----+----|----+----|----+----|----+----|   180
       TTGATACCTCACTTGACCTATTTCGTCTGAGGTCCTCTCCCAAATGTCACCTACCCGACCTATTTGGGGTTGTGACCTCTCGGTTGTAAA
         N  Y  G  V  N  W  I  K  Q  T  P  G  E  G  L  Q  W  M  G  W  I  N  P  N  T  G  E  P  T  F
         _____                                                     52A
            CDR1                              40                  50     _____
                                                                              CDR2

GATGATGACTTCAAGGGACGATTTGCCTTCTCTCTTTGGAATCCTCTGCCAGCACTGCCTTTTGCAGATCAGCAACCTCAAAAATGAGGAC
       ----+----|----+----|----+----|----+----|----+----|----+----|----+----|----+----|----+----|   270
       CTACTACTGAAGTTCCCTGCTAAACGGAAGAGAGAAACCTTAGGAGACGGTCGTGACGGAAAACGTCTAGTCGTTGGAGTTTTTACTCCTG
         D  D  D  F  K  G  R  F  A  F  S  L  E  S  S  A  S  T  A  F  L  Q  I  S  N  L  K  N  E  D
         60                                               70                  80      82A B C

ATGGGTACACATATTTCTGTTCAAGATCGAGGGTAAAAACGAAGCCTGGTTTGCTTATTGGGGCCAAGGGACTCTGGTCACTGTCTCTGAA
       ----+----|----+----|----+----|----+----|----+----|----+----|----+----|----+----|----+----|   360
       TACCCATGTGTATAAAGACAAGTTCTAGCTCCCATTTTTGCTTCGGACCAAACGAATAACCCGGTTCCCTGAGACCAGTGACAGAGACTT
         M  G  T  Y  F  C  S  R  S  R  G  K  N  E  A  W  F  A  Y  W  G  Q  G  T  L  V  T  V  S  E
                     90             _____              110
                                              CDR3                 100A B K
```

```
GATGTTGTGATGACCCAAACTCCACTCTCCCTGCCTGTCAGTCTTGGAGATCAAGCCTCCATCTCTTGCAGATCTAGTCAGAGCCTTGTA
------+---------+---------+---------+---------+---------+---------+---------+---------+    90
CTACAACACTACTGGGTTTGAGGTGAGAGGGACGGACAGTCAGAAGTTCGAGGTAGAGAACGTCTAGATCAGTCTCGGAACAT
 D  V  V  M  T  Q  T  P  L  S  L  P  V  S  L  G  D  Q  A  S  I  S  C  R  S  S  Q  S  L  V
                      10                    20                        27A B C
                                                                     HRNTYLH CDR1
                                                                      (underline indicates CDR1 starting at position R S S Q S L V)

CACAGAAATGGAAACCTATTTACATTGGTACCTGCAGAAGCCAGGCCAGTCTCCTGATCTACACAGTTTCAACCGATTT
------+---------+---------+---------+---------+---------+---------+---------+   180
GTGTCTTTACCTTTGGATAAATGTAACCATGGACGTCTTCGGTCCGGTCAGAGGACTAGATGTGTCAAAGTTGGCTAAA
 D  E  H  R  N  G  N  T  Y  L  H  W  Y  L  Q  K  P  G  Q  S  P  K  L  L  I  Y  T  V  S  N  R  F
       30                         40                         50
       CDR1                                                  CDR2

TCTGGGGTCCCAGACAGGTTCAGTGGCAGTGGATCAGGGACAGATTTCACACTCAAGATCAGTAGAGTGGAGGCTGAGGATCTGGGACTT
------+---------+---------+---------+---------+---------+---------+---------+---------+    270
AGACCCCAGGGTCTGTCCAAGTCACCGTCACCTAGTCCCTGTCTAAAGTGTGAGTTCTAGTCATCTCCACTCCGACTCCTAGACCCTGAA
 S  G  V  P  D  R  F  S  G  S  G  S  G  T  D  F  T  L  K  I  S  R  V  E  A  E  D  L  G  L
    60                         70                         80

TATTTCTGCTCTCAAAGTTCACATGTTCCTCCCACGTTCGGTGCTGGGACCAAGCTGGAGATCTAAC
------+---------+---------+---------+---------+---------+------    337
ATAAAGACGAGAGTTTCAAGTGTACAAGGAGGGTGCAAGCCACGACCCTGGTTCGACCTCTAGATTG
 Y  F  C  S  Q  S  S  H  V  P  P  T  F  G  A  G  T  K  L  E  I
          90                        100
          CDR3
```

FIG. 1B cLL1VH

```
         PstI
CAGGTCCAACTGCAG CAGTCTGGACCTGAGCTGAAGAAGCCTGGAGAGACAGTCAAGGTCACCTGCAAGACTTCTGGATATACCTTCACA
---------------+---------------+---------------+---------------+---------------+---------------  90
GTCCAGGTTGACGTC GTCAGACCTGGACTCGACTTCTTCGGACCTCTCTGTCAGTTCCAGTGGACGTTCTGAAGACCTATATGGAAGTGT

Q  V  Q  L  Q  Q  S  G  P  E  L  K  K  P  G  E  T  V  K  V  T  C  K  T  S  G  Y  T  F  T        30

AACTATGGAGTGAACTGGATAAAGCAGACTCCAGGAGAGGGTTTACAGTGGATGGGCTGGATAAACCCCAACACTGGAGAGCCAACATTT
---------------+---------------+---------------+---------------+---------------+---------------  180
TTGATACCTCACTTGACCTATTTCGTCTGAGGTCCTCTCCCAAATGTCACCTACCCGACCTATTTGGGGTTGTGACCTCTCGGTTGTAAA

N  Y  G  V  N  W  I  K  Q  T  P  G  E  G  L  Q  W  M  G  W  I  N  P  N  T  G  E  P  T  F        59
    CDR1                                            CDR2

GATGATGACTTCAAGGGACGATTTGCCTTCTCTTTGGAATCCTCTGCCAGCACTGCCTTTTTGCAGATCAGCAACCTCAAAAATGAGGAC
---------------+---------------+---------------+---------------+---------------+---------------  270
CTACTACTGAAGTTCCCTGCTAAACGGAAGAGAAACCTTAGGAGACGGTCGTGACGGAAAAACGTCTAGTCGTTGGAGTTTTACTCCTG

D  D  D  F  K  G  R  F  A  F  S  L  E  S  S  A  S  T  A  F  L  Q  I  S  N  L  K  N  E  D        89
         CDR3

BstEII
ATGGGTACATATTTCTGTTCAAGATCGAGGGGTAAAAACGAAGCCTGGTTTGCTTATTGGGGCCAAGGGACTCTGGTCACCGTCTCCTCA
---------------+---------------+---------------+---------------+---------------+---------------  360
TACCCATGTATAAAGACAAGTTCTAGCTCCCCATTTTTGCTTCGGACCAAACGAATAACCCCGGTTCCCTGAGACCAGTGGCAGAGGAGT

M  G  T  Y  F  C  S  R  S  R  G  K  N  E  A  W  F  A  Y  W  G  Q  G  T  L  V  T  V  S  S       113
                       CDR3
```

FIG. 2A cLL1Vk

```
        PvuII
GACATCCAGCTGACCCAAACTCCACTCTCCCTGCCTGTCAGTCTTGGAGATCAAGCTCTCCATCTCTTGCAGATCTAGTCAGAGCCTTGTA        90
     ---+---------+---------+---------+---------+---------+---------+---------+---------+
CTGTAGGTCGACTGGGTTTGAGGTGAGAGGGACGGACAGTCAGAACCTCTAGTTCGAGAGGTAGAGAACGTCTAGATCAGTCGGAACAT

D  I  Q  L  T  Q  T  P  L  S  L  P  V  S  L  G  D  Q  A  S  I  S  C  R  S  S  Q  S  L  V

CACAGAAATGGAAACACCTATTTACATTGGTACCTGCAGAAGCCAGGCCAGTCTCCAAAGCTCCTGATCTACACAGTTTCCAACCGATTT      270
     ---+---------+---------+---------+---------+---------+---------+---------+---------+
GTGTCTTTACCTTTGTGGATAAATGTAACCATGGACGTCTTCGGTCCGGTCAGAGGTTTCGAGGACTAGATGTGTCAAAGGTTGGCTAAA

H  R  N  G  N  T  Y  L  H  W  Y  L  Q  K  P  G  Q  S  P  K  L  L  I  Y  T  V  S  N  R  F
    CDR1                                                                  CDR2

TCTGGGGTCCCAGACAGGTTCAGTGGCAGTGGATCAGGGACAGATTTCACACTGAAGATCAGTAGAGTGGAGGCTGAGGATCTGGGACTT      270
     ---+---------+---------+---------+---------+---------+---------+---------+---------+
AGACCCCAGGGTCTGTCCAAGTCACCGTCACCTAGTCCCTGTCTAAAGTGTGAGTTCTAGTCATCTCACCTCCGACTCCTAGACCCTGAA

S  G  V  P  D  R  F  S  G  S  G  S  G  T  D  F  T  L  K  I  S  R  V  E  A  E  D  L  G  L

BglII/BclI
TATTTCTGCTCTCAAAGTTCACATGTTCCTCCCACGTTCGGTGCTGGGACCAAGCTGGAGATCAAACGT                            339
     ---+---------+---------+---------+---------+---------+---------+-
ATAAAGACGAGAGTTTCAAGTGTACAAGGAGGGTGCAAGCCACGACCCTGGTTCGACCTCTAGTTTGCA

Y  F  C  S  Q  S  S  H  V  P  P  T  F  G  A  G  T  K  L  E  I  K  R
        CDR3
```

FIG. 2B

```
RF-TS3    QVQLVQSGSELKKPGASVKVSCKASGYTFTSYAMNWVRQA   40
cLL1VH    QVQLQ···P····ET···T·······N·GV··IK·T       40
hLL1VH    QVQLQ·····················N·GV··IK··       40

RF-TS3    PGQGLEWMGWINTNTGNPTYAQGFTGRFVFSLDTSVSTAY   79
cLL1VH    ··E··Q······P····E··FDDD·K···A···ES·A···F  79
hLL1VH    ····Q·······P····E··FDDD·K···A·········   79

RF-TS3    LQISSLKADDTAVYYCAREDSNGYKIFDY              102
cLL1VH    ····N··NE·MGT·F·S·SRGKNEAW·A·              102
hLL1VH    ···············F·S·SRGKNEAW·A·             102

NEW

```
HF-21/28    DVVMTQSPLSLPVTLGQPASISQ RSSQSLVHSDGNTYLN W    35
cLl1Vk      DIQL··T·····S·GDQ····· ···RN········H ·    35
hLl1Vk      DIQL················· ···RN········H ·    35

HF-21/28    FQQRPGQSPRRLIY KVSNRDS GVPDRFSGSGSGTDFTLKI    75
cLl1Vk      YL·K····KL···· ·T···F· ··················    75
hLl1Vk      ·············· ·T···F· ··················    75

HF-21/28    SRVEAEDVGVYYC MQGTHWPFT FGQGTRLEI           106
cLl1Vk      ·L·L·F·S·SS·V·P ···A··K···IKR               108
hLl1Vk      ·····F·S·SS·V·P ···A······IKR               108
```

· denotes the amino acid is identical to the one shown in the first row

FIG.3B hLL1VH

```
CAGGTCCAACTGCAGCAATCTGGGTCTGAGTTGAAGAAGCCTGGGGCCTCAGTGAAGGTTTCCTGCAAGGCTTCACT    90
------+---------+---------+---------+---------+---------+---------+---------+
GTCCAGGTTGACGTCGTTAGACCCAGACTCAACTTCTTCGGACCCCGGAGTCACTTCCAAAGGACGTTCCGAAGTGA

Q  V  Q  L  Q  Q  S  G  S  E  L  K  K  P  G  A  S  V  K  V  S  C  K  A  S  G  Y  T  F  T    30
```

```
AACTATGGAGTGAACTGGATAAAGCAGGCCCCTGGACAAGGGCTTGAGTGGATGGGCTGGATAAACCCCAACACTT   180
------+---------+---------+---------+---------+---------+---------+---------+
TTGATACCTCACTTGACCTATTTCGTCCGGGGACCTGTTCCCGAACTCACCTACCCGACCTATTTGGGGTTGTGTAAA

N  Y  G  V  N  W  I  K  Q  A  P  G  Q  G  L  Q  W  M  G  W  I  N  P  N  T  G  E  P  T  F    59
 ‾‾‾‾‾‾‾‾‾‾‾‾‾‾                                        ‾‾‾‾‾‾‾‾‾‾‾‾‾‾‾‾‾‾‾‾‾‾‾‾
     CDR1                                                          CDR2
```

```
GATGATGACTTCAAGGGACGATTTGCCTTCTCCTTGGACACCTCTGTCAGCACGGCATATCTCCAGATCAGCAGCAC   270
------+---------+---------+---------+---------+---------+---------+---------+
CTACTACTGAAGTTCCCTGCTAAACGGAAGAGGAACCTGTGGAGACAGTCGTGCCGTATAGAGGTCTAGTCGTCGTG

D  D  D  F  K  G  R  F  A  F  S  L  D  T  S  V  S  T  A  Y  L  Q  I  S  S  L  K  A  D  D    89
 ‾‾‾‾‾‾‾‾‾‾‾‾‾‾‾‾‾
      CDR3
```

```
ACTGCCGTGTATTTCTGTTCAAGATCGAGGGGTAAAAACGAAGCCTGGTTTGCTTATTGGGGCCAAGGAGCCTGTCACCGTCTCCTCA   360
------+---------+---------+---------+---------+---------+---------+---------+---------+
TGACGGCACATAAAGACAAGTTCTAGCTCCCCATTTTGCTTCGGACCAAACGAATAACCCCGGTTCCTCGGACCAGTGGCAGAGGAGT

T  A  V  Y  F  C  S  R  S  R  G  K  N  E  A  W  F  A  Y  W  G  Q  G  S  L  V  T  V  S  S    113
             ‾‾‾‾‾‾‾‾‾‾‾‾‾‾‾‾‾‾‾‾‾‾‾‾‾‾‾‾‾
                      CDR3
```

FIG. 4A hLL1Vk

```
      GACATCCAGCTGACTCAGTCTCCACTCTCCCTGCCCGTCACCCTTGGACAGCCGGCCTCCATCTCCTGCAGATCAAGTCAGAGCCTTGTA      90
      ---------+---------+---------+---------+---------+---------+---------+---------+---------+
      CTGTAGGTCGACTGAGTCAGAGGTGAGAGGGACGGGCAGTGGGAACCTGTCGGCGGAGGTAGTAGAGGACGTCTAGTTCAGTCTCGGAACAT

D  I  Q  L  T  Q  S  P  L  S  L  P  V  T  L  G  Q  P  A  S  I  S  C  R  S  S  Q  S  L  V

CACAGAAATGGAAACACCTATTTACATTGGTTTCAGCAGAGGCCAGGCCAATCTCCAAGGCTCCTGATCTACACAGTTTCCAACCGATTT      280
      ---------+---------+---------+---------+---------+---------+---------+---------+---------+
      GTGTCTTTACCTTTGTGGATAAATGTAACCAAAGTCGTCTCCGGTTAGAGGTTCCGAGGACTAGATGTGTCAAAGGTTGGCTAAA

H  R  N  G  N  T  Y  L  H  W  F  Q  Q  R  P  G  Q  S  P  R  L  L  I  Y  T  V  S  N  R  F
       ────────CDR1────────                                            ────────CDR2

TCTGGGGTCCCAGACAGATTCAGCGGCAGTGGGTCAGGGACACTGATTTCACACTGAAAATCAGCAGGGTGGAGGCTGAGGATGTTGGGGTT      55
      ---------+---------+---------+---------+---------+---------+---------+---------+---------+
      AGACCCCAGGGTCTGTCTAAGTCGCCGTCACCCAGTCCCTGTGACTAAAGTGTGACTTTTAGTCGTCCCACCTCCGACTCCTACAACCCAA     270

S  G  V  P  D  R  F  S  G  S  G  S  G  T  D  F  T  L  K  I  S  R  V  E  A  E  D  V  G  V

TATTTCTGCTCTCAAAGTTCACATGTTCCTCCCACGTTCGGTGCTGGGACCACGACTGGAGATCAAACGT                           85
      ---------+---------+---------+---------+---------+---------+---------+
      ATAAAGACGAGAGTTTCAAGTGTACAAGGAGGGTGCAAGCCACGACCCTGGTGCTGACCTCTAGTTTGCA                           339

Y  F  C  S  Q  S  S  H  V  P  P  T  F  G  A  G  T  R  L  E  I  K  R                           108
            ────────CDR3────────
```

FIG. 4B

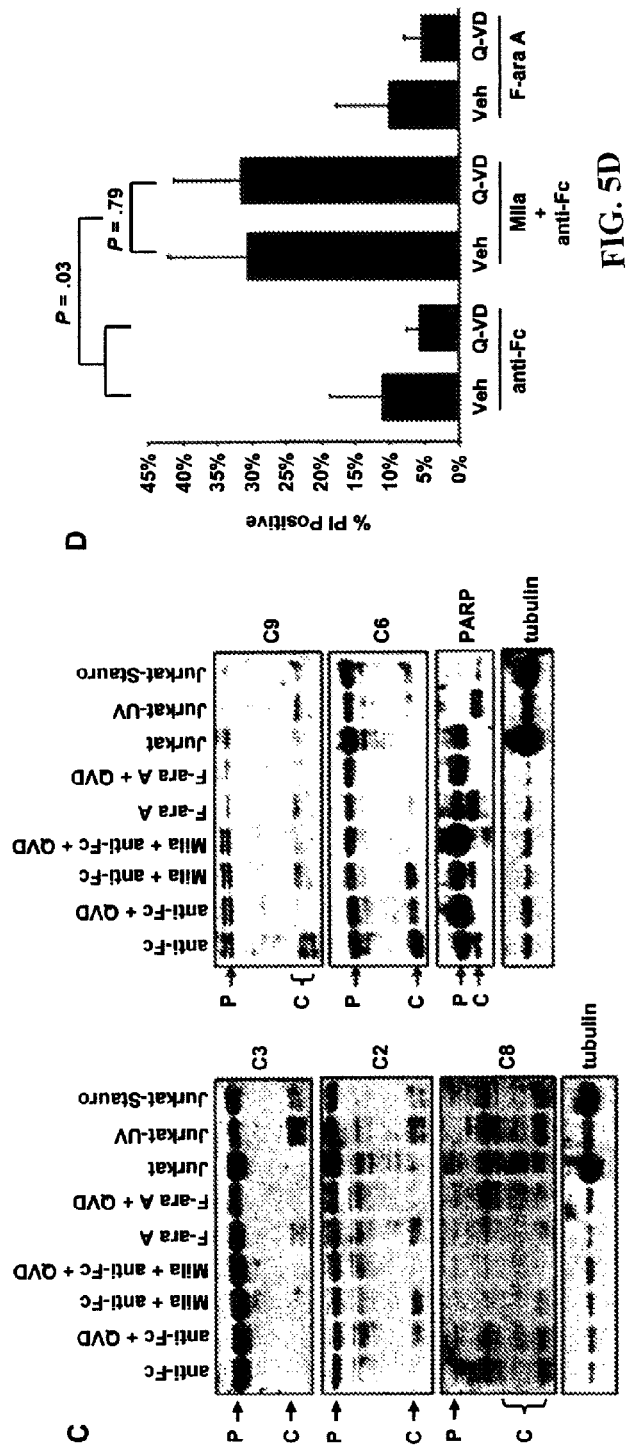
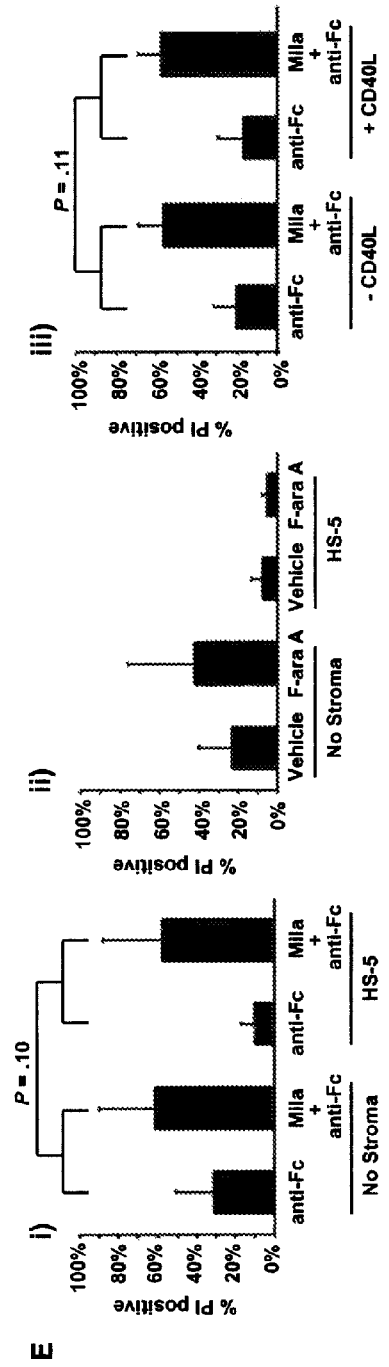
FIG. 5C
FIG. 5D
FIG. 5E

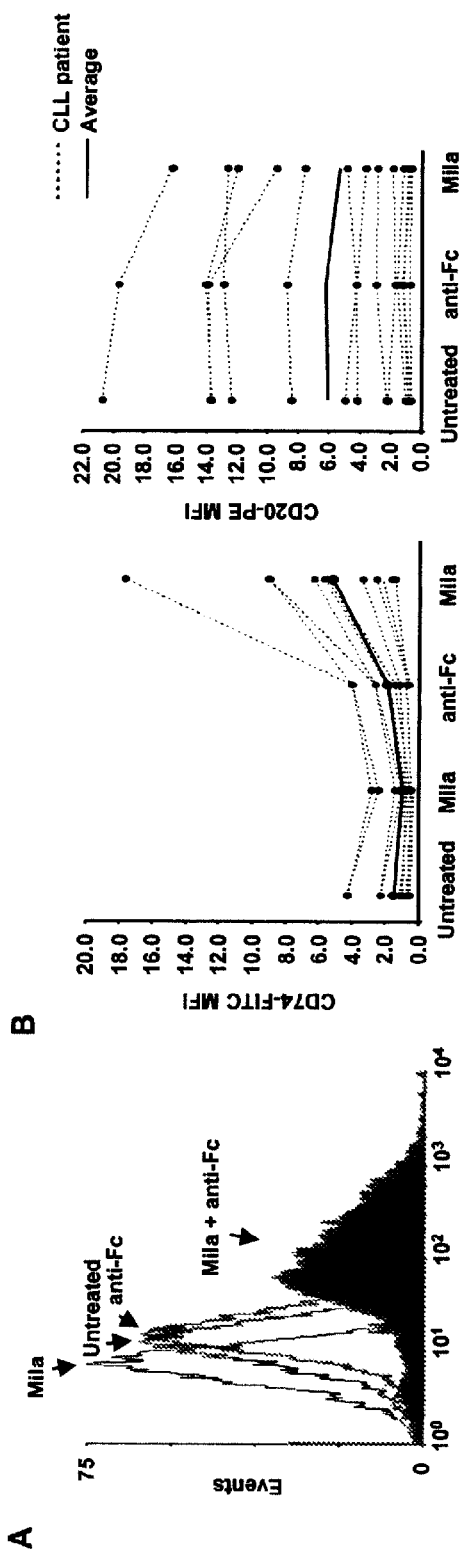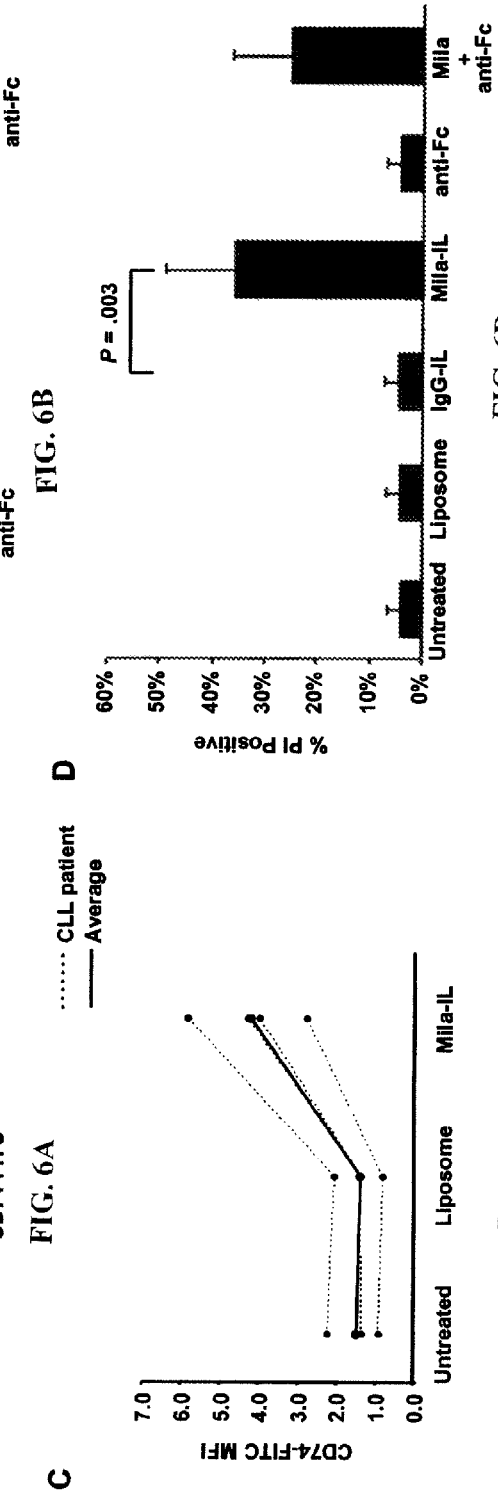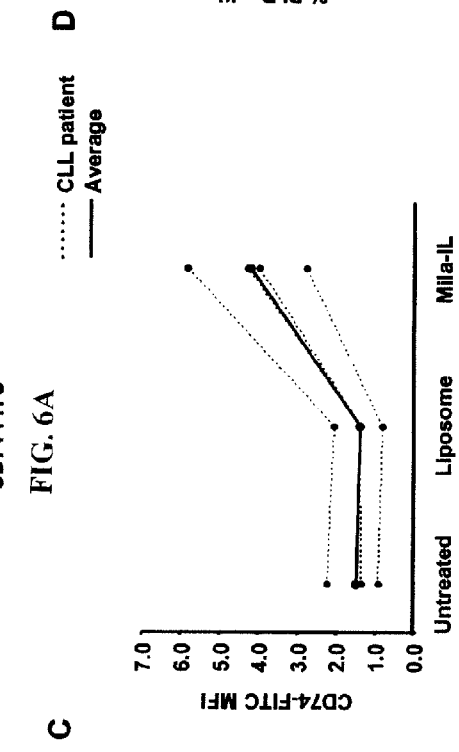
FIG. 6A
FIG. 6B
FIG. 6C
FIG. 6D ic Acid.

ANTI-CD74 IMMUNOCONJUGATES AND METHODS OF USE

CROSS-REFERENCE TO RELATED APPLICATIONS

This application is a continuation-in-part of application Ser. No. 10/706,852, filed Nov. 12, 2003, which claimed the benefit under 35 U.S.C. 119(e) of provisional application Ser. No. 60/478,830, filed on Jun. 17, 2003, and which was a continuation-in-part of application Ser. No. 10/314,330, filed on Dec. 9, 2002, which was a continuation of application Ser. No. 09/965,796, filed on Oct. 1, 2001, which was a continuation of application Ser. No. 09/307,816, filed on May 10, 1999, now U.S. Pat. No. 6,306,393. U.S. Ser. No. 10/706,852 was also a continuation-in-part of application Ser. No. 10/350,096, filed on Jan. 24, 2003, which was a continuation of application Ser. No. 09/590,284, filed on Jun. 9, 2000, now U.S. Pat. No. 7,074,403. U.S. Ser. No. 10/706,852 was also a continuation-in-part of application Ser. No. 10/377,122, filed on Mar. 3, 2003, now U.S. Pat. No. 7,312,318, which claimed the benefit of provisional application Ser. No. 60/360,259, filed on Mar. 1, 2002.

This application claims the benefit under 35 U.S.C. 119(e) to provisional application Ser. No. 61/265,999, filed Dec. 2, 2009. All of the above-identified applications and patents are incorporated herein by reference in their entireties.

FEDERALLY FUNDED RESEARCH

This work was supported in part by National Cancer Institute grants CA95426, CA103985 and CA81534-02. The Federal Government may have certain rights in the invention.

Sequence Listing

The instant application contains a Sequence Listing which has been submitted via EFS-Web and is hereby incorporated by reference in its entirety. Said ASCII copy, created on Jun. 29, 2010, is named IMM323US.txt and is 21,952 bytes in size.

FIELD OF THE INVENTION

The present invention concerns compositions and methods of use of liposomes attached to targeting molecules, such as antibodies, antibody fragments or antibody fusion proteins. More particularly, the antibodies, fragments or fusion proteins may bind to a tumor associated antigen, infectious disease associated antigen or other disease associated antigen. Even more particularly, the targeting molecule may bind to the invariant chain (Ii) of the HLA-DR complex, also known as CD74. An exemplary anti-CD74 antibody is milatuzumab (hLL1). The antibody conjugated liposome is of use for the treatment of a variety of diseases, such as autoimmune disease, immune dysregulation disease, cancer, lymphoma, leukemia, chronic lymphocytic leukemia, follicular lymphoma, diffused large B cell lymphoma, multiple myeloma or non-Hodgkin's lymphoma.

BACKGROUND

Liposomes have been used as carriers for therapeutic agents, where antibodies may be conjugated to the liposome to provide specific targeting of the liposome/agent complex to a diseased cell or tissue. (See, e.g., Xu et al., Mol. Cancer. Ther., 1:337-346 (2002); Torchilin, et al., Proc. Nat'l. Acad. Sci., 10: 6039 (2003); U.S. Pat. No. 6,165,440; U.S. Pat. No. 5,702,727; U.S. Pat. No. 5,620,708; U.S. Pat. No. 5,565,215; U.S. Pat. No. 6,530,944; U.S. Pat. No. 6,562,318; U.S. Pat. No. 6,558,648; and U.S. Pat. No. 6,395,276). The antibody or antibodies of choice for targeting purposes may bind to a known tumor associated antigen (TAA) or to an antigen associated with infectious diseases or other disease states.

One such tumor-associated antigen is CD74, which is an epitope of the major histocompatibility complex (MHC) class II antigen invariant chain, Ii, present on the cell surface and taken up in large amounts of up to $8 \times 10^6$ molecules per cell per day (Hansen et al., 1996, Biochem. J., 320: 293-300). CD74 is present on the cell surface of B-lymphocytes, monocytes and histocytes, human B-lymphoma cell lines, melanomas, T-cell lymphomas and a variety of other tumor cell types. (Hansen et al., 1996, Biochem. J., 320: 293-300) CD74 associates with $\alpha/\beta$ chain MHC II heterodimers to form MHC II $\alpha\beta$Ii complexes that are involved in antigen processing and presentation to T cells (Dixon et al., 2006, Biochemistry 45:5228-34; Loss et al., 1993, J Immunol 150:3187-97; Cresswell et al., 1996; Cell 84:505-7).

CD74 also plays an important role in cell proliferation and survival. Binding of the CD74 ligand, macrophage migration inhibitory factor (MIF), to CD74 activates the MAP kinase cascade and promotes cell proliferation (Leng et al., 2003, J Exp Med 197:1467-76). Binding of MIF to CD74 also enhances cell survival through activation of NF-κB and Bcl-2 (Lantner et al., 2007, Blood 110:4303-11).

Murine LL1 (mLL1 or murine anti-CD74 antibody) is a specific monoclonal antibody (mAb) reactive with CD74. Cell surface-bound LL1 is rapidly internalized to the lysosomal compartment and quickly catabolized, much faster than other antibodies, such as anti-CD19 or anti-CD22 (Hansen et al., 1996, Biochem. J., 320: 293-300). LL1 was reported to exhibit the highest rate of accumulation inside B cells of any of the antibodies tested (Griffiths et al., 2003, Clin Cancer Res 9:6567-71).

Murine LL1 was developed by fusion of mouse myeloma cells with splenocytes from BALB/c mice immunized with preparations from the Raji B-lymphoma cell line (called EPB-1 in Pawlak-Byczkowska et al., Can. Res., 49: 4568 (1989)). The clinical use of mLL1, just as with most other promising murine antibodies, has been limited by the development in humans of a human anti-mouse antibody (HAMA) response. A HAMA response is generally not observed following injection of mLL1 Fab', as evidenced in a bone marrow imaging study using an mLL1 Fab' labeled with $^{99m}$Tc. Juweid et al., Nuc. Med. Comm. 18: 142-148 (1997). However, in some therapeutic and diagnostic uses, a full-length anti-CD74 antibody may be preferred. This use of the full-length anti-CD74 antibody can limit the diagnostic and therapeutic usefulness of such antibodies and antibody conjugates, not only because of the potential anaphylactic problem, but also as a major portion of the circulating conjugate may be complexed to and sequestered by the circulating anti-mouse antibodies. Although the use of antibody fragments of mLL1 may circumvent the problems of immunogenicity, there are circumstances in which whole IgG is more desirable and the induction of cellular immunity is intended for therapy or enhanced antibody survival time. In general, HAMA responses pose a potential obstacle to realizing the full diagnostic and therapeutic potential of murine anti-CD74 antibodies. Therefore, the development of immunoconjugates that include chimeric, humanized and human anti-CD74 binding molecules, (e.g., antibodies and fragments thereof, antibody fusion proteins thereof, multivalent and/or multi-specific antibodies and fragments thereof), would be extremely useful for therapy and diagnosis, with reduced production of human anti-mouse antibodies.

SUMMARY

Disclosed is a composition that includes an immunoconjugate, where the immunoconjugate includes an anti-CD74 binding molecule conjugated to a liposome. In preferred embodiments, the anti-CD74 binding molecule is an antibody, antigen-binding antibody fragment, antibody fusion protein or multispecific antibody or fragment thereof. In certain embodiments, the composition may also comprise one or more additional effector molecules, such as a radionuclide, a chemotherapeutic agent, a toxin, an enzyme, an immunomodulator or a second antibody or fragment thereof. The additional effector(s) may be contained within the liposome or attached to the anti-CD74 antibody. However, the skilled artisan will realize that methods of therapy of common disease states, such as cancer, may involve the administration to a subject of two or more different therapeutic agents (effector molecules) concurrently, consecutively or separately.

The anti-CD74 binding molecule may be conjugated or linked to the liposome by a number of linkages including sulfide linkages, hydrazone linkages, hydrazine linkages, ester linkages, amido linkages, amino linkages, imino linkages, thiosemicarbazone linkages, semicarbazone linkages, oxime linkages, and carbon-carbon linkages. A sulfide linkage may be preferred, where the binding molecule may include disulfide linkages, which may be reduced to provide free thiol groups.

The composition may include additional binding molecules, (e.g., antibodies or fragments thereof that bind to CD19, CD20, CD22, CD30, CD33, CD52, CD80, HLA-DR, MUC1, TAC, IL-6, tenascin, VEGF, placental growth factor, carbonic anhydrase IX, and mixtures thereof). The additional binding molecules may be covalently or non-covalently associated with any component of the composition (e.g., the liposome).

To facilitate conjugation to the anti-CD74 binding molecule, the lipid molecules making up the liposome may contain one or more groups capable of reacting with the anti-CD74 binding molecule, such as nucleophilic carbons, (e.g., at a distal terminus). In one embodiment, the lipid is polyethyleneglycol (PEG)-maleimide and the anti-CD74 binding molecule reacts via free thiol groups with the maleimide group. In addition to maleimide groups, other groups for conjugating binding molecules may include vinylsulfones.

The composition may include therapeutic or diagnostic agents, which may be covalently, non-covalently, or otherwise associated with any component of the composition. For example, the therapeutic or diagnostic agent may be covalently linked to the anti-CD74 binding molecule. Alternatively, the therapeutic or diagnostic agent may be covalently linked to the liposome or non-covalently or otherwise associated with the liposome.

The effector may comprise any number of therapeutic or diagnostic agents. For example, the effector may include a drug, prodrug, toxin, enzyme, radioisotope, immunomodulator, cytokine, hormone, binding molecule (e.g., an antibody), or an oligonucleotide molecule (e.g., an antisense molecule or a gene). Antisense molecules may include antisense molecules that correspond to bcl-2 or p53. The effector may include aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, Pseudomonas exotoxin, and Pseudomonas endotoxin, or combinations thereof. In certain embodiments, the effector includes FUdR, or FUdR-dO.

The composition may also include one or more hard acid chelators or soft acid chelators. For example, the chelator may include NOTA, DOTA, DTPA, TETA, Tscg-Cys, or Tsca-Cys. In certain embodiments, the chelators may form complexes with cations selected from Group II, Group III, Group IV, Group V, transition, lanthanide or actinide metal cations, or mixtures thereof. Alternatively, the cations may be covalently, non-covalently, or otherwise associated with any component of the complex. In certain embodiments, the composition includes cations selected from Tc, Re, Bi, Cu, As, Ag, Au, At, or Pb.

The composition may also include a nuclide (e.g., a radionuclide). The nuclide may be selected from a number of nuclides including $^{8}F$, $^{32}P$, $^{33}P$, $^{45}Ti$, $^{47}Sc$, $^{52}Fe$, $^{59}Fe$, $^{62}Cu$, $^{64}Cu$, $^{67}Ga$, $^{67}Ga$, $^{68}Ga$, $^{75}Se$, $^{77}As$, $^{86}Y$, $^{89}Sr$, $^{89}Zr$, $^{90}Y$, $^{99}Tc$, $^{99m}Tc$, $^{99}Mo$, $^{99m}Tc$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-158}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, or $^{225}Ac$.

Where the effector is an enzyme, suitable enzymes may include carboxylesterases, glucuronidases, carboxypeptidases, beta-lactamases, phosphatases, and mixtures thereof. Where the effector is an immunomodulator, suitable immunomodulators may include IL-1, IL-2, IL-3, IL-6, IL-10, IL-12, IL-18, IL-21, interferon-α, interferon-β, interferon-γ, G-CSF, GM-CSF, and mixtures thereof. The effector may also include an anti-angiogenic agent, e.g., angiostatin, endostatin, basculostatin, canstatin, maspin, anti-VEGF binding molecules, anti-placental growth factor binding molecules, or anti-vascular growth factor binding molecules.

Preferably, the anti-CD74 binding molecule may be LL1 or a fragment thereof, although any anti-CD74 binding molecule is suitable. For example, production of monoclonal antibodies is well known in the art. See Harlow & Lane (eds), Antibodies. A Laboratory Manual, Cold Spring Harbor Laboratory, NY. However, human, chimeric, or humanized derivatives of LL1 or fragments thereof may be particularly suitable. Derivatives of LL1 are described in U.S. Pat. No. 7,312,318 and U.S. Patent Application Ser. No. 60/360,259, filed Mar. 1, 2002, which are incorporated herein by reference in their entireties. The anti-CD74 binding molecule or fragment thereof may be monoclonal.

The anti-CD74 binding molecule may include a human, chimeric, or humanized anti-CD74 antibody or fragment thereof. For example, a binding molecule may contain the CDRs of the light and heavy chain variable regions of a murine anti-CD74 antibody. A humanized anti-CD74 antibody or fragment may include the complementarity-determining regions (CDRs) of murine anti-CD74 (mLL1) and human antibody constant and framework (FR) region sequences, which may be substituted with at least one amino acid from corresponding FRs of a murine antibody. An antibody or fragment may include a humanized IgG1.

An anti-CD74 binding molecule may be a chimeric anti-CD74 antibody or fragment thereof and may include the light and heavy chain variable regions of a murine anti-CD74 antibody, attached to human antibody constant regions. A chimeric antibody or fragment thereof may include a chimeric IgG1 or fragment thereof.

The anti-CD74 binding molecule may be selected such that the binding of the molecule or fragment thereof to CD74 competes with or is blocked by an antibody or fragment thereof specific for CD74, such as the LL1 antibody. Alternatively, the binding molecule may be selected such that the binding molecule binds to the same epitope of CD74 as an antibody or fragment thereof specific for CD74, such as the LL1 antibody. In still other alternatives, the binding molecule may be selected to be internalized by Raji lymphoma cells in culture. In another embodiment, an anti-CD74 binding molecule, such as an antibody or fragment thereof, may be selected such that it induces apoptosis of Raji cells in cell culture when cross-linked with goat antisera reactive with the Fc of a murine IgG 1 antibody.

The anti-CD74 binding molecule may also include a fragment which includes a $F(ab')_2$, Fab, scFv, Fv, or a fusion protein utilizing part or all of the light and heavy chains of the $F(ab')_2$, Fab, scFv, or Fv, such that the fragment is capable of binding to CD74. The binding molecule may be selected or designed to be multivalent, or multivalent and multispecific. The fragments may form a bispecific binding molecule or a diabody. In one embodiment, the binding molecule includes a fusion protein that includes four or more Fvs, or Fab' s of the antibodies or fragments thereof. In a further embodiment, the binding molecule includes a fusion protein that includes one or more Fvs or Fab' s of an anti-CD74 antibody or fragment thereof, and one or more Fvs or Fab's from an antibody specific for a tumor cell marker that is not a CD74 antigen. For example, the tumor cell marker may include a B-cell lineage antigen such as CD19, CD20, or CD22. Alternatively, the tumor cell marker may include HLA-DR, CD30, CD33, CD52, MUC1 or TAC.

The anti-CD 74 binding molecule may include human constant regions of IgG1, IgG2a, IgG3, or IgG4.

Also disclosed is a method for treating and/or diagnosing a disease or disorder that includes administering to a patient a therapeutic and/or diagnostic composition. The therapeutic and/or diagnostic composition includes any of the aforementioned compositions, generally a composition that includes: (1) one or more anti-CD74 binding molecules or fragments thereof conjugated to a liposome; (2) a pharmaceutically acceptable excipient; and (3) optionally an effector molecule (e.g., a therapeutic or diagnostic agent). Typically, the composition is administered to the patient intravenously, intramuscularly or subcutaneously at a dose of 20-5000 mg.

In preferred embodiments, the disease or disorder is associated with CD74-expressing cells and may be a cancer, an immune dysregulation disease, an autoimmune disease, an organ-graft rejection, a graft-versus-host disease, a solid tumor, non-Hodgkin's lymphoma, Hodgkin's lymphoma, multiple myeloma, a B-cell malignancy, or a T-cell malignancy. A B-cell malignancy may-include indolent forms of B-cell lymphomas, aggressive forms of B-cell lymphomas, chronic lymphatic leukemias, acute lymphatic leukemias, and/or multiple myeloma. Solid tumors may include melanomas, carcinomas, sarcomas, and/or gliomas. A carcinoma may include renal carcinoma, lung carcinoma, intestinal carcinoma, stomach carcinoma, breast carcinoma, prostate cancer, ovarian cancer, and/or melanoma.

In one embodiment, the composition may comprise an agent for photodynamic therapy, e.g., a photosensitizer such as a benzoporphyrin monoacid ring A (BDP-MA), tin etiopurpurin (SnET2), sulfonated aluminum phthalocyanine (AISPc), or lutetium texaphyrin (Lutex). The method may also include administering an irradiating light source to the targeted cells or tissue. In certain embodiments, photodynamic therapy may be used diagnostically as well as therapeutically.

The method may include administering a composition that includes a diagnostic nuclide, e.g., $^{18}F$, $^{52}Fe$, $^{62}Cu$, $^{46}Cu$, $^{67}Cu$, $^{67}Ga$, $^{68}Ga$, $^{86}Y$, $^{89}Zr$, $^{94}Tc$, $^{94m}Tc$, $^{99m}Tc$, $^{111}In$, $^{123}I$, $^{124}I$, $^{125}I$, $^{131}I$. Typically, the diagnostic nuclide will emit 25-4000 keV gamma particles and/or positrons.

The method may include administering a composition that includes a diagnostic agent, which can be used to perform positron emission tomography (PET), such as $^{18}F$ or $^{68}Ga$. As such, the method may include performing positron-emission tomography (PET).

The method may include administering a composition that includes one or more image enhancing agents, e.g., gadolinium ions, lanthanum ions, manganese ions, iron, chromium, copper, cobalt, nickel, fluorine, dysprosium, rhenium, europium, terbium, holmium, neodymium, or mixtures thereof. As such, the method may include performing an imaging technique such as magnetic resonance imaging (MRI).

The method may include administering a composition that includes one or more radioopaque agents or contrast agents such as barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof. The method may include performing an X-ray or computed tomography (CT).

The method may include administering a composition that includes one or more ultrasound contrast agents, such as dextran or a liposome (e.g., a gas-filled liposome). The method may include performing an ultrasound procedure.

In addition to the aforementioned procedures, the method may also include performing an operative, intravascular, laparoscopic, or endoscopic procedure, before, simultaneously with, or after the immunoconjugate or composition is administered.

The method may also include administering a second or additional composition that includes a therapeutic or diagnostic agent, where the second or additional composition is administered before, simultaneously, or after the first composition is administered. The second or additional composition may include any of the aforementioned compositions. In one embodiment the second or additional composition includes an anti-CD74 binding molecule conjugated to a therapeutic or diagnostic agent. The therapeutic or diagnostic agent may comprise any of the aforementioned drugs, prodrugs, toxins, enzymes, radioisotopes, immunomodulators, cytokines, hormones, antibodies, binding molecules, oligonucleotides, chelators, cations, therapeutic nuclides, agents for photodynamic therapy, diagnostic nuclides, image enhancing agents, radioopaque agents, and/or contrasting agents. The method may also include performing a PET, MRI, X-ray, CT, ultrasound, operative, intravascular, laparoscopic, or endoscopic procedure.

Also disclosed are methods of preparing the aforementioned compositions (e.g., an anti-CD74 immunoconjugate by mixing one or more amphiphilic lipids to form a liposome and contacting the liposome with an anti-CD74 binding molecule, (e.g., an antibody or fragment thereof)). In one example, the lipid contains nucleophilic carbons (e.g., within a maleimide group), and the binding molecule contains free thiol groups (e.g., disulfides treated with a reducing agent). The method may include mixing the composition with one or more therapeutic or diagnostic agents, which may be covalently, non-covalently, or otherwise associated with any component of the composition.

Also disclosed is a kit that includes any of the aforementioned compositions or the components sufficient for preparing any of the aforementioned compositions. Typically, the kit includes instructions for administering the compositions or, where applicable, instructions for preparing the compositions.

BRIEF DESCRIPTION OF THE DRAWINGS

FIG. 1. DNA and amino acid sequences of the murine LL1 heavy and light chain variable regions. FIG. 1A shows DNA (SEQ ID NO: 7) and amino acid (SEQ ID NO: 8) sequences of $LL1V_H$. FIG. 1B shows DNA (SEQ ID NO: 9) and amino acid (SEQ ID NO: 10) sequences of the $LL1V_k$. Amino acid sequences encoded by the corresponding DNA sequences are given as one-letter codes below the nucleotide sequence. Numbering of the nucleotide sequence is on the right side. The amino acid residues in the CDR regions are shown in bold and underlined. Kabat's Ig molecule numbering is used for amino acid residues as shown by the numbering above the amino acid residues. The residues numbered by a letter following a particular digit indicates the insertion residues defined by Kabat numbering scheme. The insertion residues numbered with a letter have the same preceding digit. For example, residues 82A, 82B and 82C in FIG. 1A are indicated as 82A, B, and C.

FIG. 2. DNA and amino acid sequences of chimeric LL1 (cLL1) heavy and light chain variable region (see, U.S. Pat. No. 7,312,318). FIG. 2A shows DNA (SEQ ID NO: 11) and amino acid (SEQ ID NO: 12) sequences of $cLL1 V_H$. FIG. 2B shows double-stranded DNA (SEQ ID NO: 13) and amino acid (SEQ ID NO: 14) sequences of $cLL1V_k$. Amino acid sequences encoded by the corresponding DNA sequences are given as one-letter codes. The amino acid residues in the CDR regions are shown in bold and underlined. The numbering of nucleotides and amino acids is same as that in FIG. 1.

FIG. 3. Alignment of amino acid sequences of light and heavy chain variable regions of a human antibody, cLL1 and hLL1. FIG. 3A shows the $V_H$ amino acid sequence alignment of the human antibody RF-TS3 (SEQ ID NO: 15), cLL1 (SEQ ID NO: 12) and hLL1 (SEQ ID NO: 18). FIG. 3B shows the $V_k$ amino acid sequence alignment of the human antibody HF-21/28 (SEQ ID NO: 16), cLL1 (SEQ ID NO: 14) and hLL1 (SEQ ID NO: 20). Dots indicate the residues in cLL1 that are identical to the corresponding residues in the human antibodies. Boxed regions represent the CDR regions. Both N- and C-terminal residues (underlined) of cLL1 are fixed by the staging vectors used and not compared with the human antibodies. Kabat's Ig molecule number scheme is used as in FIG. 1.

FIG. 4. DNA and amino acid sequences of humanized LL1 (hLL1) heavy and light chain variable regions. FIG. 4A shows the DNA (SEQ ID NO: 17) and amino acid (SEQ ID NO: 18) sequences of $hLL1 V_H$. FIG. 4B shows the DNA (SEQ ID NO: 19) and amino acid (SEQ ID NO: 20) sequences of $hLL1V_k$. Amino acid sequences encoded by the corresponding DNA sequences are given as one letter codes. The amino acid residues in the CDR regions are shown in bold and underlined. Kabat's Ig molecule numbering scheme is used for amino acid residues as in FIG. 1.

FIG. 5. Milatuzumab mediates direct cytotoxicity in CLL cells. FIG. 5C. Immunoblots for caspases-2, 3, 8, 6, 9 and PARP in whole cell lysates isolated from CLL cells treated with anti-Fc, 5 μg/mL mila+anti-Fc, or 5 μM fludarabine in the presence or absence of 20 μM caspase inhibitor, QVD-OPH, for 24 hours. Jurkat cells treated with UV or staurosporine were used as controls for caspase cleavage. Pro-caspase (P) and cleaved (C) forms are indicated. FIG. 5D. Viability of CLL patient cells by PI staining treated with anti-Fc, 5 μg/mL mila+anti-Fc, or 5 μM fludarabine in the presence or absence of 20 μM caspase inhibitor, Q-VD-OPH, for 24 hours (N=5; P=0.03). FIG. 5E. (panel i) Viability of CLL patient cells treated with anti-Fc alone or 5 μg/mL mila+anti-Fc in the presence or absence of stroma co-culture. After 6 hours in drug, cells were washed and cultured in fresh media alone or in the presence of HS-5 stromal cells. Viability was determined by PI staining after 48 hours of co-culture (N=11; P=0.10). (panel ii) Viability of CLL patient cells treated with vehicle or 1 μM 2-F-ara A in the presence or absence of stroma co-culture. After 6 hours in drug cells were washed and cultured in fresh media alone or in the presence of HS-5 cells. Viability by PI staining was determined after 48 hours of co-culture (N=6). (panel iii) Viability of CLL patient cells treated with anti-Fc alone or 5 μg/mL mila+anti-Fc in the presence or absence of 500 ng/mL soluble CD40L. Viability by PI staining was determined at 48 hours (N=17; P=0.11).

FIG. 6. Milatuzumab immunoliposome increases CD74 on the surface of CLL cells and induces cell death. FIG. 6A. Mean fluorescent intensity of surface CD74 in CLL patient cells either untreated, treated with 25 μg/mL anti-Fc, or 5 μg/mL milatuzumab with or without 25 μg/mL anti-Fc for 1 hour. Histogram shown is representative of 14 patients. FIG. 6B. Lett. Mean fluorescent intensity of CD74 in CLL patient cells either untreated, treated with 25 μg/mL anti-Fc, or 5 μg/mL milatuzumab with or without 25 μg/mL anti-Fc for 1 hour (N=14; P=0.0003). Right. Mean fluorescent intensity of CD20 in CLL patient cells either untreated, or treated with 5 μg/mL milatuzumab with or without 25 μg/mL anti-Fc for 1 hour (N=14; P=0.14). FIG. 6C. Mean fluorescent intensity of CD74 in CLL patient cells either untreated, or treated with empty liposome or milatuzumabimmunoliposome (mila-IL) for 1 hour (N=4; P=0.0003). FIG. 6D. Viability by PI staining in CLL patient cells either untreated, or treated with empty liposome, IgG-immunoliposome (IgG-IL), mila-IL, 25 μg/mL anti-Fc or 5 μg/mL milatuzumab with 25 μg/mL anti-Fc for 24 hours (N=11; P=0003).

DETAILED DESCRIPTION

Definitions

Figures 5A, 5B:
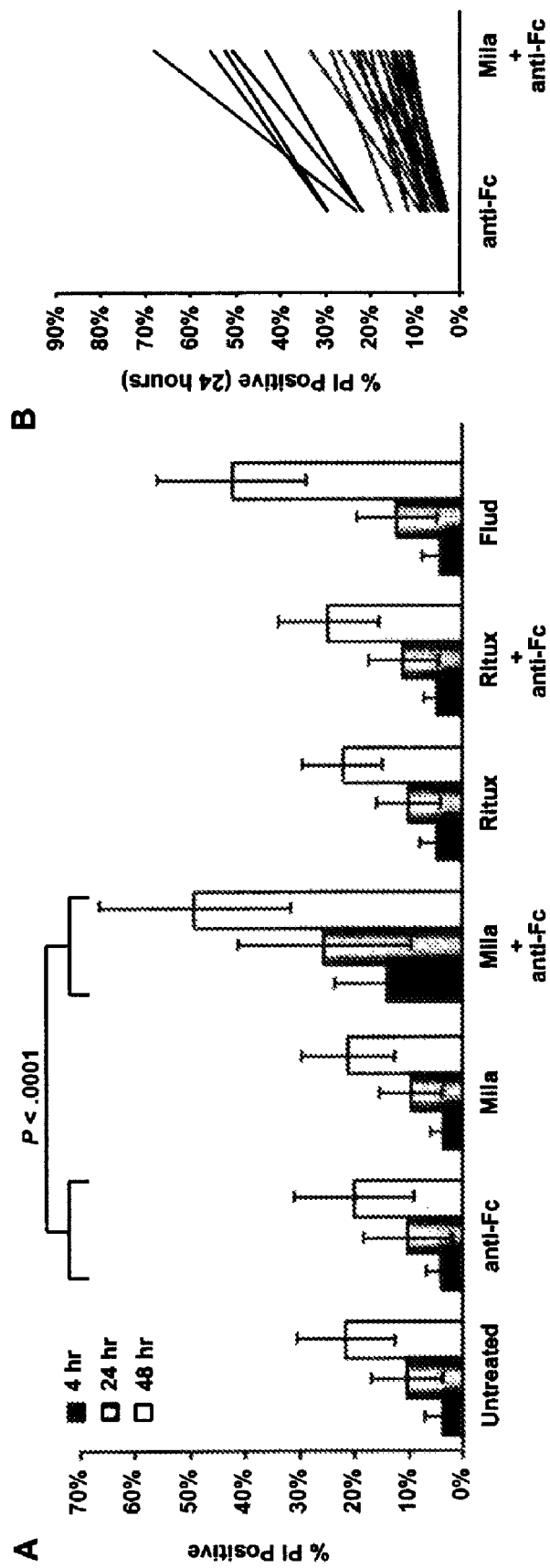
FIG. 5A. Viability of CLL patient cells at 4, 24 and 48 hours by propidium iodide (PI) staining. Cells were untreated, treated with goat anti-human Fc crosslinker alone, or treated with 5 μg/mL milatuzumab (Mita) or 10 gg/mL rituximab (Ritux) in the presence or absence of anti-Fc crosslinker (in five times excess of binding antibody) (N=26; P<0.0001 for anti-Fc vs. mila+anti-Fc). Y-axis indicates the percent of PI positive cells and the active metabolite of fludarabine (2-F-ara A; Flud) was used as a positive control for cell death.
FIG. 5B. Viability of CLL patient cells at 24 hours by PI staining (N=26 from FIG. 5A; each line represents individual patient sample).

The following definitions are provided to facilitate understanding of the disclosure herein. Where a term is not specifically defined, it is used in accordance with its plain and ordinary meaning.

As used herein, the terms "a", "an" and "the" may refer to either the singular or plural, unless the context otherwise makes clear that only the singular is meant.

As used herein, the term "about" means plus or minus ten percent (10%) of a value. For example, "about 100" would refer to any number between 90 and 110.

A "binding molecule," as used herein, is any molecule that can specifically or selectively bind to an antigen. A binding molecule may include an antibody or a fragment thereof. An anti-CD74 binding molecule is a molecule that binds to the CD74 antigen, such as an anti-CD74 antibody or fragment thereof. Other anti-CD74 binding molecules may also include multivalent molecules, multispecific molecules (e.g., diabodies), fusion molecules, aptimers, avimers, or other naturally occurring or recombinantly created molecules.

An "antibody" refers to a full-length (i.e., naturally occurring or formed by normal immunoglobulin gene fragment recombinatorial processes) immunoglobulin molecule (e.g., an IgG antibody) or an immunologically active (i.e., antigen-binding) portion of an immunoglobulin molecule, like an antibody fragment.

An "antibody fragment" is a portion of an antibody such as $F(ab')_2$, $F(ab)_2$, Fab', Fab, Fv, scFv, single domain antibodies (DABs or VHHs) and the like, including half-molecules of IgG4 (van der Neut Kolfschoten et al. (Science 2007; 317(14 September):1554-1557). Regardless of structure, an antibody fragment binds with the same antigen that is recognized by the intact antibody. For example, an anti-CD74 antibody fragment binds with an epitope of CD74. The term "antibody fragment" also includes isolated fragments consisting of the variable regions, such as the "Fv" fragments consisting of the variable regions of the heavy and light chains, recombinant single chain polypeptide molecules in which light and heavy chain variable regions are connected by a peptide linker ("scFv proteins"), and minimal recognition units consisting of the amino acid residues that mimic the hypervariable region.

A "chimeric antibody" is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A "humanized antibody" is a recombinant protein in which the CDRs from an antibody from one species; e.g., a rodent antibody, are transferred from the heavy and light variable chains of the rodent antibody into human heavy and light variable domains. The constant domains of the antibody molecule are derived from those of a human antibody.

A "human antibody" is an antibody obtained from transgenic mice that have been genetically engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. (See, e.g., McCafferty et al., Nature 348:552-553 (1990) for the production of human antibodies and fragments thereof in vitro, from immunoglobulin variable domain gene repertoires from unimmunized donors). In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see, e.g. Johnson and Chiswell, Current Opinion in Structural Biology 3:5564-571 (1993). Human antibodies may also be generated by in vitro activated B cells. (See, U.S. Pat. Nos. 5,567,610 and 5,229,275).

An "effector" is an atom, molecule, or compound that brings about a chosen result. An effector may include a therapeutic agent and/or a diagnostic agent.

A "therapeutic agent" is an atom, molecule, or compound that is useful in the treatment of a disease. Examples of therapeutic agents include but are not limited to antibodies, antibody fragments, drugs, toxins, enzymes, nucleases, hormones, immunomodulators, antisense oligonucleotides, chelators, boron compounds, photoactive agents, dyes and radioisotopes.

A "diagnostic agent" is an atom, molecule, or compound that is useful in diagnosing a disease. Useful diagnostic agents include, but are not limited to, radioisotopes, dyes, contrast agents, fluorescent compounds or molecules and enhancing agents (e.g., paramagnetic ions). Preferably, the diagnostic agents are selected from the group consisting of radioisotopes, enhancing agents, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), DOTA, NOTA, NETA, porphyrins, polyamines, crown ethers, bis-thiosemicarbazones, polyoximes, and like groups known to be useful for this purpose. Chelates are coupled to the peptide antigens using standard chemistries. The chelate is normally linked to the antibody by a group which enables formation of a bond to the molecule with minimal loss of immunoreactivity and minimal aggregation and/or internal cross-linking. Other, more unusual, methods and reagents for conjugating chelates to antibodies are disclosed in U.S. Pat. No. 4,824,659. Particularly useful metal-chelate combinations include 2-benzyl-DTPA and its monomethyl and cyclohexyl analogs, used with diagnostic isotopes in the general energy range of 60 to 4,000 keV. Some useful diagnostic nuclides may include, such as $^{18}F$, $^{52}Fe$, $^{62}Cu$, $^{64}Cu$, $^{67}Cu$, $^{67}Ga$, $^{68}Ga$, $^{86}Y$, $^{89}Zr$, $^{94}Tc$, $^{94m}Tc$, $^{99m}Tc$, or $^{111}In$. The same chelates, when complexed with non-radioactive metals, such as manganese, iron and gadolinium are useful for MRI, when used along with the antibodies and liposomes described herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT may be used. In certain embodiments, chelating moieties may be used to attach a PET imaging agent, such as an Al-$^{18}$F complex, to a targeting molecule for use in PET analysis (see, e.g., U.S. Pat. Nos. 7,563,433 and 7,597,876, the Examples section of each of which is incorporated herein by reference.)

An "immunoconjugate" is a conjugate of a binding molecule (e.g., an antibody) with an atom, molecule, or a higher-ordered structure (e.g., with a liposome), a therapeutic agent, or a diagnostic agent. The diagnostic agent can comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. A "naked antibody" is an antibody that is not conjugated to any other agent.

As used herein, the term "antibody fusion protein" is a recombinantly produced antigen-binding molecule in which an antibody or antibody fragment is linked to another protein or peptide, such as the same or different antibody or antibody fragment or a DDD or AD peptide. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators and toxins. One preferred toxin comprises a ribonuclease (RNase), preferably a recombinant RNase.

A "multispecific antibody" is an antibody that can bind simultaneously to at least two targets that are of different structure, e.g., two different antigens, two different epitopes on the same antigen, or a hapten and/or an antigen or epitope. A "multivalent antibody" is an antibody that can bind simultaneously to at least two targets that are of the same or different structure. Valency indicates how many binding arms or sites the antibody has to a single antigen or epitope; i.e., monovalent, bivalent, trivalent or multivalent. The multivalency of the antibody means that it can take advantage of multiple interactions in binding to an antigen, thus increasing the avidity of binding to the antigen. Specificity indicates how many antigens or epitopes an antibody is able to bind; i.e., monospecific, bispecific, trispecific, multispecific. Using these definitions, a natural antibody, e.g., an IgG, is bivalent because it has two binding arms but is monospecific because it binds to one epitope. Multispecific, multivalent antibodies are constructs that have more than one binding site of different specificity. For example, a diabody, where one binding site reacts with one antigen and the other with another antigen.

A "bispecific antibody" is an antibody that can bind simultaneously to two targets which are of different structure. Bispecific antibodies (bsAb) and bispecific antibody fragments (bsFab) may have at least one arm that specifically binds to, for example, a B-cell, T-cell, myeloid-, plasma-, and mast-cell antigen or epitope and at least one other arm that specifically binds to a targetable conjugate that bears a therapeutic or diagnostic agent. A variety of bispecific antibodies can be produced using molecular engineering.

Preparation of Monoclonal Antibodies

The immunoconjugates and compositions described herein may include monoclonal antibodies. Rodent monoclonal antibodies to specific antigens may be obtained by methods known to those skilled in the art. (See, e.g., Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991)).

General techniques for cloning murine immunoglobulin variable domains have been disclosed, for example, by the publication of Orlandi et al., Proc. Nat'l Acad. Sci. USA 86: 3833 (1989). Techniques for constructing chimeric antibodies are well known to those of skill in the art. As an example, Leung et al., Hybridoma 13:469 (1994), disclose how they produced an LL2 chimera by combining DNA sequences encoding the $V_k$ and $V_H$ domains of LL2 monoclonal antibody, an anti-CD22 antibody, with respective human and IgG$_1$ constant region domains. This publication also provides the nucleotide sequences of the LL2 light and heavy chain variable regions, $V_k$ and $V_H$, respectively. Techniques for producing humanized antibodies are disclosed, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993).

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody can also be humanized by replacing the sequences of the murine FR in the variable domains of the chimeric antibody with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. (See, e.g., Tempest et al., Biotechnology 9:266 (1991) and Verhoeyen et al., Science 239: 1534 (1988)).

A fully human antibody, i.e., human anti-CD74 antibodies or other human antibodies, such as anti-CD22, anti-CD19, anti-CD23, anti-CD20 or anti-CD21 antibodies for combination therapy with humanized, chimeric or human anti-CD74 antibodies, can be obtained from a transgenic non-human animal. (See, e.g., Mendez et al., Nature Genetics, 15: 146-156, 1997; U.S. Pat. No. 5,633,425.) Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the µ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

In various embodiments, the claimed methods and compositions may utilize any of a variety of antibodies known in the art. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Particular antibodies that may be of use for therapy of cancer within the scope of the claimed methods and compositions include, but are not limited to, LL1 (anti-CD74), LL2 and RFB4 (anti-CD22), RS7 (anti-epithelial glycoprotein-1 (EGP-1)), PAM4 and KC4 (both anti-mucin), MN-14 (anti-carcinoembryonic antigen (CEA, also known as CD66e), Mu-9 (anti-colon-specific antigen-p), Immu 31 (an anti-alpha-fetoprotein), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb) and hL243 (anti-HLA-DR). Such antibodies are known in the art (e.g., U.S. Pat. Nos. 5,686,072; 5,874,540; 6,107,090; 6,183,744; 6,306, 393; 6,653,104; 6,730.300; 6,899,864; 6,926,893; 6,962,702;

7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU31 (U.S. Pat. No. 7,300,655), hLL1 (U.S. Pat. No. 7,312,318), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. Provisional Patent Application 61/145,896), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections.

Production of Antibody Fragments

Antibody fragments which recognize specific epitopes can be generated by known techniques. The antibody fragments are antigen binding portions of an antibody, such as F(ab)$_2$, Fab', Fab, Fv, scFv and the like. Other antibody fragments include, but are not limited to: the F(ab')$_2$ fragments which can be produced by pepsin digestion of the antibody molecule and the Fab' fragments, which can be generated by reducing disulfide bridges of the F(ab')$_2$ fragments. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are disclosed in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991).

An antibody fragment can be prepared by known methods, for example, as disclosed by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

A single complementarity-determining region (CDR) is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. (See, e.g., Larrick et al., Methods: A Companion to Methods in Enzymology 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec Immunol 2006, 43:1912-19; Tanha et al., J. Biol. Chem. 2001, 276:24774-780).

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., Molecular Cloning, A laboratory manual, $2^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, J Nucl Med 41:355-62; Hinton et al., 2006, J Immunol 176:346-56; Petkova et al. 2006, Int Immunol 18:1759-69; U.S. Pat. No. 7,217,797).

Anti-CD74 Antibodies

The anti-CD74 binding molecules of the present immunoconjugates and compositions may contain specific murine CDRs that have binding affinity for the CD74 antigen. For example, the anti-CD74 binding molecules may be humanized, chimeric or human antibodies, and they may contain the amino acids of the CDRs of a murine anti-CD74 antibody, (e.g., the murine anti-CD74 antibody, LL1). Humanized, chimeric, and human anti-CD74 antibody or fragments thereof are described in U.S. Pat. No. 7,312,318, the Examples section of which is incorporated herein by reference.

Where the anti-CD74 antibody is humanized, it may contain CDRs of a light chain variable region of a murine anti-CD74 antibody (e.g., a CDR1 having an amino acid sequence RSSQSLVHRNGNTYLH (SEQ ID NO:1); a CDR2 having an amino acid sequence TVSNRFS (SEQ ID NO:2); and a CDR3 having an amino acid sequence SQSSHVPPT (SEQ ID NO:3)). The humanized anti-CD74 antibody or fragment may include the heavy chain variable region of the humanized antibody, which may include CDRs of a heavy chain variable region of a murine anti-CD74 antibody (e.g., a CDR1 having an amino acid sequence NYGVN (SEQ ID NO:4); a CDR2 having an amino acid sequence WINPNTGEPTFDDDFKG (SEQ ID NO:5); and a CDR3 having an amino acid sequence SRGKNEAWFAY (SEQ ID NO:6)). The humanized anti-CD74 antibody or fragment thereof may include light and heavy chain variable regions including complementarity-determining regions (CDRs) of murine anti-CD74 (mLL1) and human antibody constant and framework (FR) region sequences, which may be substituted with at least one amino acid from the corresponding FRs of the murine antibody. In one embodiment, the substituted amino acid may be selected from amino acid residue 2, 3, 4, 46, 87 and 100 of the murine LL1 light chain variable region (FIG. 3B), and amino acid residues 5, 37, 38, 46, 68, 91 and 93 of the murine heavy chain variable region (FIG. 3A). In another embodiment, the antibody or fragment thereof comprises a heavy chain variable region of FIG. 4A and a light chain variable region of FIG. 4B. In a further embodiment, the antibody or fragment thereof may comprise a light and heavy chain constant region of a human antibody or a portion thereof. The antibody or fragment may include a humanized IgG1.

Where the anti-CD74 binding molecule includes a chimeric anti-CD74 antibody, the chimeric anti-CD74 antibody or fragment thereof may include a light chain variable region of a murine anti-CD74 antibody (e.g., a CDR1 having an amino acid sequence RSSQSLVHRNGNTYLH (SEQ ID NO:1); a CDR2 having an amino acid sequence TVSNRFS (SEQ ID NO:2); and a CDR3 having an amino acid sequence SQSSHVPPT (SEQ ID NO:3)). In another embodiment, the chimeric anti-CD74 antibody or fragment thereof may include a heavy chain variable region of a murine anti-CD74 antibody (e.g., a CDR1 having an amino acid sequence NYGVN (SEQ ID NO:4); a CDR2 having an amino acid sequence WINPNTGEPTFDDDFKG (SEQ ID NO:5); and a CDR3 having an amino acid sequence SRGKNEAWFAY (SEQ ID NO:6)). In a further embodiment, the chimeric anti-CD74 antibody or fragment thereof may include the framework (FR) regions of a murine anti-CD74 antibody and the light and heavy chain constant regions of a human antibody. Alternatively, the chimeric antibody or fragment thereof may include a heavy chain variable region of FIG. 2A and a light chain variable region of FIG. 2B. The chimeric antibody or fragment thereof may be a chimeric IgG1 or fragment thereof.

Where the anti-CD74 binding molecule is a human anti-CD74 antibody, the human anti-CD74 antibody or fragment thereof may include a light chain variable region of the human anti-CD74 antibody (e.g., a CDR1 having an amino acid sequence RSSQSLVHRNGNTYLH (SEQ ID NO:1); a CDR2 having an amino acid sequence TVSNRFS (SEQ ID NO:2); and a CDR3 having an amino acid sequence SQSSHVPPT (SEQ ID NO:3)). In one embodiment, the human anti-CD74 antibody or fragment thereof may include a heavy chain variable region of the human antibody which may include CDRs of a heavy chain variable region of a murine anti-CD74 antibody (e.g., a CDR1 having an amino acid sequence NYGVN (SEQ ID NO:4); a CDR2 having an amino acid sequence WINPNTGEPTFDDDFKG (SEQ ID NO:5); and a CDR3 having an amino acid sequence SRGKNEAWFAY (SEQ ID NO:6)). The human antibody or fragment thereof may be a human IgG1.

Anti-CD74 antibodies of use may include murine, chimeric, humanized or human antibodies that contain CDRs other than the CDRs of the LL1 antibody recited above, but which still block or compete for binding to CD74 with a murine, chimeric or humanized LL1 antibody. For example, such anti-CD74 antibodies may bind to the same epitope of CD74 as the LL1 antibody. Antibody binding competition experiments are well known in the art and may be performed using any standard techniques, described in more detail below.

Multispecific and Multivalent Antibodies

The anti-CD74 binding molecule of the present immunoconjugates and compositions, as well as other binding molecules with different specificities for use in combination therapy, can also include multispecific antibodies (comprising at least one binding site to a CD74 epitope or antigen and at least one binding site to another epitope on CD74 or another antigen), and multivalent antibodies (comprising multiple binding sites to the same epitope or antigen), or the antibodies can be both multivalent and multispecific.

A preferred binding molecule of the present immunoconjugates or compositions is a fusion protein, which contains two or more Fvs, Fab's or other antigen-binding fragments of a humanized, chimeric, human or murine anti-CD74 antibody. Another preferred antibody fusion protein contains one or more Fvs, Fab's or other antigen-binding fragments of a humanized, chimeric, human or murine anti-CD74 antibody and one or more Fvs, Fab's or other fragments from antibodies specific for another antigen that is a tumor cell marker other than CD74. For example, the non-CD74 antigen may be expressed by the CD74-expressing cells and may include a tumor marker selected from a B-cell lineage antigen, (e.g., CD19, CD20, or CD22 for the treatment of B-cell malignancies). The non-CD74 antigen may also be expressed on other CD74 positive cells that cause other types of malignancies, such as S100 in melanoma, etc. Further, the tumor cell marker may be a non-B-cell lineage antigen selected from the group consisting of HLA-DR, CD30, CD33, CD52 MUC1 and TAC. Other useful antigens may include carbonic anhydrase IX, B7, CCCL19, CCCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM-6, alpha-fetoprotein (AFP), VEGF (e.g. AVASTIN®, fibronectin splice variant), ED-B fibronectin (e.g., L19), EGP-1, EGP-2 (e.g., 17-1A), EGF receptor (ErbB1) (e.g., ERBITUX®), ErbB2, ErbB3, Factor H, FHL-1, Flt-3, folate receptor, Ga 733, GROB, HMGB-1, hypoxia inducible factor (HIF), HM1.24, HER-2/neu, insulin-like growth factor (ILGF), IFN-γ, IFN-α, IFN-β, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5, placental growth factor (P1GF), PSA (prostate-specific antigen), PSMA, pancreatic cancer mucin, PAM4 antigen, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), VEGFR, RANTES, T101, as well as cancer stem cell antigens, complement factors C3, C3a, C3b, C5a, C5, and an oncogene product.

Methods for producing bispecific antibodies include engineered recombinant antibodies which have additional cysteine residues so that they crosslink more strongly than the more common immunoglobulin isotypes. (See, e.g., FitzGerald et al, Protein Eng. 10(10):1221-1225, (1997)). Another approach is to engineer recombinant fusion proteins linking two or more different single-chain antibody or antibody fragment segments with the needed dual specificities. (See, e.g., Coloma et al., Nature Biotech. 15:159-163, (1997)). A variety of bispecific antibodies can be produced using molecular engineering. In one form, the bispecific antibody may consist of, for example, an scFv with a single binding site for one antigen and a Fab fragment with a single binding site for a second antigen. In another form, the bispecific antibody may consist of, for example, an IgG with two binding sites for one antigen and two scFv with two binding sites for a second antigen.

Conjugated Anti-CD74 Antibodies

In various embodiments, a conjugated anti-CD74 antibody or fragment thereof may be used to prepare an immunoconjugate or composition. In certain embodiments, additional amino acid residues may be added to either the N- or C-terminus of the anti-CD74 antibody or fragment. The additional amino acid residues may comprise a peptide tag, a signal peptide, a cytokine, an enzyme (for example, a pro-drug activating enzyme), a hormone, a peptide toxin, such as *Pseudomonas* exotoxin, a peptide drug, a cytotoxic protein or other functional proteins. As used herein, a functional protein is a protein that has a biological function.

In another embodiment, a liposome may be conjugated to the anti-CD74 antibody or fragment thereof. See, e.g., Ryser et al., Proc. Natl. Acad. Sci. USA, 75:3867-3870, 1978, U.S. Pat. No. 4,699,784 and U.S. Pat. No. 4,046,722, which are incorporated herein by reference. Conjugation preferably does not significantly affect the binding specificity or affinity of the anti-CD74 antibody or fragment thereof. In certain embodiments, the liposome may be covalently or non-covalently attached to one or more therapeutic and/or diagnostic agents.

In one embodiment, drugs, toxins, radioactive compounds, enzymes, hormones, cytotoxic proteins, chelates, cytokines and other functional agents may be conjugated to the anti-CD74 antibody or fragment, preferably through covalent attachments to the side chains of the amino acid residues of the anti-CD74 antibody or fragment, for example amine, carboxyl, phenyl, thiol or hydroxyl groups. Various conventional linkers may be used for this purpose, for example, diisocyanates, diisothiocyanates, bis(hydroxysuccinimide) esters, carbodiimides, maleimide-hydroxysuccinimide esters, glutaraldehyde and the like. Conjugation of agents to the anti-CD74 antibody or fragment thereof preferably does not significantly affect the protein's binding specificity or affinity to its target.

In still other embodiments, antibody-directed delivery of therapeutics or prodrug polymers to in vivo targets can be combined with antibody delivery of radionuclides, such that combination chemotherapy and radioimmunotherapy is achieved. Each therapeutic agent can be conjugated to a targetable conjugate and administered simultaneously, or the nuclide can be given as part of a first targetable conjugate and the drug given in a later step as part of a second targetable conjugate.

Avimers

In certain embodiments, the binding moieties described herein may comprise one or more avimer sequences. Avimers are a class of binding proteins somewhat similar to antibodies in their affinities and specificities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains, that may exhibit improved affinity (in some cases sub-nanomolar) and specificity compared with single-epitope binding proteins. (Id.) In various embodiments, avimers may be attached to, for example, DDD and/or AD sequences for use in the claimed methods and compositions. Additional details concerning methods of construction and use of avimers are disclosed, for example, in U.S. Patent Application Publication Nos. 20040175756 (now abandoned), 20050048512 (now abandoned), 20050053973 (now abandoned), 20050089932 and 20050221384 (now abandoned), the Examples section of each of which is incorporated herein by reference.

Phage Display

Certain embodiments of the claimed compositions and/or methods may concern binding peptides and/or peptide mimetics of various target molecules or target-binding molecules. Binding peptides may be identified by any method known in the art, including but not limiting to the phage display technique. Various methods of phage display and techniques for producing diverse populations of peptides are well known in the art. For example, U.S. Pat. Nos. 5,223,409; 5,622,699 and 6,068,829 disclose methods for preparing a phage library. The phage display technique involves genetically manipulating bacteriophage so that small peptides can be expressed on their surface (Smith and Scott, 1985, Science 228:1315-1317; Smith and Scott, 1993, Meth. Enzymol. 21:228-257). In addition to peptides, larger protein domains such as single-chain antibodies may also be displayed on the surface of phage particles (Arap et al., 1998, Science 279: 377-380).

Targeting amino acid sequences selective for a given organ, tissue, cell type or target molecule may be isolated by panning (Pasqualini and Ruoslahti, 1996, Nature 380:364-366; Pasqualini, 1999, The Quart. J. Nucl. Med. 43:159-162). In brief, a library of phage containing putative targeting peptides is administered to an intact organism or to isolated organs, tissues, cell types or target molecules and samples containing bound phage are collected. Phage that bind to a target may be eluted from a target organ, tissue, cell type or target molecule and then amplified by growing them in host bacteria.

In certain embodiments, the phage may be propagated in host bacteria between rounds of panning. Rather than being lysed by the phage, the bacteria may instead secrete multiple copies of phage that display a particular insert. If desired, the amplified phage may be exposed to the target organs, tissues, cell types or target molecule again and collected for additional rounds of panning. Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998, Smith et al., 1985).

In some embodiments, a subtraction protocol may be used to further reduce background phage binding. The purpose of subtraction is to remove phage from the library that bind to targets other than the target of interest. In alternative embodiments, the phage library may be prescreened against a control cell, tissue or organ. For example, tumor-binding peptides may be identified after prescreening a library against a control normal cell line. After subtraction the library may be screened against the molecule, cell, tissue or organ of interest. Other methods of subtraction protocols are known and may be used in the practice of the claimed methods, for example as disclosed in U.S. Pat. Nos. 5,840,841, 5,705,610, 5,670,312 and 5,492,807.

Aptamers

In certain embodiments, a targeting moiety of use may be an aptamer. Methods of constructing and determining the binding characteristics of aptamers are well known in the art. For example, such techniques are described in U.S. Pat. Nos. 5,582,981, 5,595,877 and 5,637,459, the Examples section of each incorporated herein by reference. Methods for preparation and screening of aptamers that bind to particular targets of interest are well known, for example U.S. Pat. No. 5,475, 096 and U.S. Pat. No. 5,270,163, the Examples section of each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S, Not all linkages in an oligomer need to be identical.

Use of Humanized, Chimeric and Human Antibody for Treatment and Diagnosis

Compositions and/or immunoconjugates comprising humanized, chimeric or human monoclonal antibodies, i.e., anti-CD74 antibodies and other antibodies described herein, are suitable for use in the therapeutic methods and diagnostic methods as described herein. Accordingly, the immunoconjugates or compositions may include naked humanized, chimeric or human antibodies or may comprise antibodies that have been conjugated to a liposome, a therapeutic agent, or a diagnostic agent. The immunoconjugates may be administered as a multimodal therapy. For example, additional therapeutic or diagnostic agents may be administered before, simultaneously, or after administration of the immunoconjugate or composition.

The efficacy of the immunoconjugates may be enhanced by supplementing the anti-CD74 binding molecules with one or more other binding molecules, (e.g., antibodies to antigens such as carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM-6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, PAM4 antigen, NCA-95, NCA-90, Ia, HM1.24, EGP-1, EGP-2, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5, and an oncogene product or HLA-DR, preferably mature HLA-DR dimer). Preferred B-cell-associated antigens include CD19, CD20, CD21, CD22, CD23, CD46, CD52, CD74, CD80 and CD5. Preferred T-cell antigens include CD4, CD8 and CD25 (the IL-2 receptor). HLA-DR antigen can be used in treatment of both B-cell and T-cell disorders. Particularly preferred B-cell antigens are CD19, CD22, CD21, CD23, CD74, CD80 and HLA-DR. Particularly preferred T-cell antigens are CD4, CD8 and CD25. CD46 is an antigen on the surface of cancer cells that block complement-dependent lysis (CDC). Preferred malignant melanoma associated antigens are MART-1, TRP-1, TRP-2 and gp100. Further, preferred multiple myeloma-associated antigens are MUC1 and CD38.

The supplemental binding molecule may be naked or conjugated with a liposome, a therapeutic agent, or a diagnostic agent, including drugs, toxins, immunomodulators, hormones, enzymes and therapeutic radionuclides. The supplemental binding molecule may be administered concurrently, sequentially, or according to a prescribed dosing regimen, with the anti-CD74 immunoconjugate.

Further contemplated herein is the administration of an immunoconjugate for diagnostic and therapeutic uses in B cell lymphomas and other disease or disorders. An immunoconjugate is a molecule comprising a binding molecule conjugated to a liposome. The immunoconjugate may be used to form a composition that further includes a therapeutic or diagnostic agent, which may include a peptide that may bear the diagnostic or therapeutic agent. An immunoconjugate retains the immunoreactivity of the binding molecule, (i.e., the antibody moiety has about the same or slightly reduced ability to bind the cognate antigen after conjugation as before conjugation).

A wide variety of diagnostic and therapeutic reagents can be used to form the immunoconjugates and compositions as described herein. Therapeutic agents include, for example, chemotherapeutic drugs such as vinca alkaloids, anthracyclines, epidophyllotoxins, taxanes, antimetabolites, alkylating agents, antibiotics, Cox-2 inhibitors, antimitotics, antiangiogenic and apoptotic agents, particularly doxorubicin, methotrexate, taxol, CPT-11, camptothecans, and others from these and other classes of anticancer agents, and the like. Other useful cancer chemotherapeutic drugs for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Additionally, a chelator such as DTPA, DOTA, TETA, or NOTA can be conjugated to one or more components of the compositions as described herein. Alternatively, a suitable peptide including a detectable label, (e.g., a fluorescent molecule), or a cytotoxic agent, (e.g., a heavy metal or radionuclide), can be covalently, non-covalently, or otherwise associated with more components of the compositions as described herein. For example, a therapeutically useful immunoconjugate can be obtained by incorporating a photoactive agent or dye in the composition as described herein. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Joni et al. (eds.), PHOTODYNAMIC THERAPY OF TUMORS AND OTHER DISEASES (Libreria Progetto 1985); van den Bergh, Chem. Britain 22:430 (1986)). Moreover, monoclonal antibodies have been coupled with photoactivated dyes for achieving phototherapy. Mew et al., J. Immunol. 130:1473 (1983); idem., Cancer Res. 45:4380 (1985); Oseroff et al., Proc. Natl. Acad. Sci. USA 83:8744 (1986); idem., Photochem. Photobiol. 46:83 (1987); Hasan et al., Prog. Clin. Biol. Res. 288:471 (1989); Tatsuta et al., Lasers Surg. Med. 9:422 (1989); Pelegrin et al., Cancer 67:2529 (1991). Endoscopic applications are also contemplated. Endoscopic methods of detection and therapy are described in U.S. Pat. Nos. 4,932, 412; 5,525,338; 5,716,595; 5,736,119; 5,922,302; 6,096,289; and 6,387,350, the Examples section of each of which is incorporated herein by reference. Thus, contemplated herein is the therapeutic use of anti-CD74 immunoconjugate compositions comprising photoactive agents or dyes, and the present diagnostic/therapeutic methods may include the diagnostic or therapeutic use of anti-CD74 immunoconjugate compositions comprising photoactive agents or dyes.

Also contemplated is the use of radioactive and non-radioactive agents as diagnostic agents in the anti-CD74 immunoconjugate compositions as described herein. A suitable non-radioactive diagnostic agent is a contrast agent suitable for magnetic resonance imaging, computed tomography or ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies described herein. (See U.S. Ser. No. 09/921,290 filed on Oct. 10, 2001, which is incorporated in its entirety by reference).

Furthermore, the anti-CD74 immunoconjugate compositions may include a radioisotope or a positron-emitter useful for diagnostic imaging. Suitable radioisotopes may include those in the energy range of 60 to 4,000 keV. Suitable radioisotopes may include $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, $^{111}$In, $^{123}$I, $^{124}$I, $^{125}$I, $^{131}$I, and like.

A toxin, such as Pseudomonas exotoxin, may also be present in the anti-CD74 immunoconjugate compositions as described herein. For example, the toxin may be complexed to or form the therapeutic agent portion of an antibody fusion protein of an anti-CD74 antibody described herein. Other toxins include ricin, abrin, ribonuclease (RNase), DNase I, Staphylococcal enterotoxin-A, pokeweed antiviral protein, gelonin, diphtheria toxin, Pseudomonas exotoxin, and Pseudomonas endotoxin. (See, e.g., Pastan et al., Cell 47:641 (1986), and Goldenberg, C A—A Cancer Journal for Clinicians 44:43 (1994)). Additional toxins suitable for use herein are known to those of skill in the art and are disclosed in U.S. Pat. No. 6,077,499, the Examples section of which is incorporated herein by reference.

An immunomodulator, such as a cytokine may also be present in the administered anti-CD74 immunoconjugate compositions as described herein. For example, an immunomodulator may be conjugated to, or form the therapeutic agent portion of an antibody fusion protein or be administered as part of the anti-CD74 immunoconjugate compositions as described herein. Suitable cytokines include, but are not limited to, interferons and interleukins, as described below.

Preparation of Immunoconjugates

The immunoconjugates described herein can be prepared by known methods of linking antibodies with lipids, carbohydrates, protein, or other atoms and molecules. For example, the binding molecules described herein can be conjugated with a liposome to form an immunoconjugate. In certain embodiments, the immunoconjugate can incorporate a therapeutic or diagnostic agent either covalently, non-covalently. Further, any of the binding molecules described herein can be further conjugated with one or more therapeutic or diagnostic agents described herein. Generally, one therapeutic or diagnostic agent may be attached to each binding molecule but more than one therapeutic agent or diagnostic agent can be attached to the same binding molecule. The antibody fusion proteins contemplated herein comprise two or more antibodies or fragments thereof and each of the antibodies that comprises this fusion protein may be conjugated with a liposome. Additionally, one or more of the antibodies of the antibody fusion protein may have one or more therapeutic of diagnostic agent attached. Further, the therapeutic do not need to be the same but can be different therapeutic agents. For example, the compositions described herein may include a drug and a radioisotope.

For example, an IgG can be radiolabeled with $^{131}$I and conjugated to a lipid, such that the IgG-lipid conjugate can form a liposome. The liposome may incorporate one or more therapeutic or diagnostic agents, (e.g., a drug such as FUdR-dO). Alternatively, in addition to the liposome, the IgG may be conjugated to $^{131}$I (e.g., at a tyrosine residue) and a drug (e.g., at the epsilon amino group of a lysine residue), and the liposome may incorporate an additional therapeutic or diagnostic agent. Therapeutic and diagnostic agents may be covalently associated with the binding molecule, (e.g., conjugated to reduced disulfide groups, carbohydrate side chains, or any other reactive group on the binding molecule. However, the skilled artisan will realize that the liposome-conjugated antibodies may be used without any additional therapeutic or diagnostic agents to induce apoptosis, as further described in the Examples below.

A liposome, therapeutic agent, or diagnostic agent can be attached at the hinge region of a reduced antibody component via disulfide bond formation. As an alternative, peptides or other molecules containing reactive moieties can be attached to an antibody component using a heterobifunctional cross-linker, such as N-succinyl 3-(2-pyridyldithio)proprionate (SPDP). Yu et al., Int. J. Cancer 56: 244 (1994). General techniques for such conjugation are well known in the art. (See, e.g., Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995)). Alternatively, the liposome, therapeutic agent, or diagnostic agent can be conjugated via a carbohydrate moiety in the Fc region of an antibody. The carbohydrate group can be used to increase the loading of the same peptide that is bound to a thiol group, or the carbohydrate moiety can be used to bind a different peptide.

Methods for conjugating peptides to antibody components via an antibody carbohydrate moiety are well known to those of skill in the art. (See, e.g., Shih et al., Int. J. Cancer 41: 832 (1988); Shih et al., Int. J. Cancer 46: 1101 (1990); and Shih et al., U.S. Pat. No. 5,057,313, all of which are incorporated in their entirety by reference). Similar chemistry can be used to conjugate one or more anti-CD74 binding molecules to one or more liposomes, therapeutic agents, or diagnostic agents. The general method involves reacting an antibody component having an oxidized carbohydrate portion with a liposome that has at least one free amine function and that is loaded with a plurality of peptide. This reaction results in an initial Schiff base (imine) linkage, which can be stabilized by reduction to a secondary amine to form the final conjugate.

The Fc region may be absent if the anti-CD74 binding molecule is an antibody fragment. However, it is possible to introduce a carbohydrate moiety into the light chain variable region of a full-length antibody or antibody fragment. (See, e.g., Leung et al., J. Immunol. 154: 5919 (1995); Hansen et al., U.S. Pat. No. 5,443,953 (1995), Leung et al., U.S. Pat. No. 6,254,868, the Examples section of each incorporated herein by reference). The engineered carbohydrate moiety may be used to attach a liposome or a therapeutic or diagnostic agent.

Liposomes

The formation of liposomes and micelles is known in the art. (See, e.g., Wrobel et al., Biochimica et Biophysica Acta, 1235:296 (1995); Lundberg et al., J. Pharm. Pharmacol., 51:1099-1105 (1999); Lundberg et al., Int. J. Pharm., 205: 101-108 (2000); Lundberg, J. Pharm. Sci., 83:72-75 (1994); Xu et al., Molec. Cancer Ther., 1:337-346 (2002); Torchilin et al., Proc. Nat'l. Acad. Sci., 100:6039-6044 (2003). See also U.S. Pat. No. 5,565,215; U.S. Pat. No. 6,379,698; and U.S. Pat. No. 6,858,226, the Examples section of each of which is incorporated herein by reference).

Immunoliposomes

The conjugation of antibodies or binding molecules to liposomes to form a targeted carrier for therapeutic or diagnostic agents has been described. (See, e.g., Bendas, Biodrugs, 15:215-224 (2001); Xu et al., Molec. Cancer Ther., 1:337-346 (2002); Torchilin et al., Proc. Nat'l. Acad. Sci., 100:6039-6044 (2003); Bally, et al., J. Liposome Res., 8:299-335 (1998); Lundberg, Int. J. Pharm., 109:73-81 (1994); Lundberg, J. Pharm. Pharmacol., 49:16-21 (1997); Lundberg, Anti-cancer Drug Design, 13:453-461 (1998). See also U.S. Pat. Nos. 6,306,393 and 7,074,403; U.S. Ser. No. 10/350,096; U.S. Ser. No. 60/138,284, filed Jun. 9, 1999, the Examples section of each of which is incorporated herein by reference.) Further details concerning exemplary methods for conjugation of antibodies or binding molecules to liposomes are disclosed in the Examples below.

Pharmaceutically Acceptable Excipients

The immunoconjugates or compositions may include one or more pharmaceutically suitable excipients, one or more additional ingredients, or some combination of these.

The immunoconjugate or compositions disclosed herein can be formulated according to known methods to prepare pharmaceutically useful compositions, whereby the immunoconjugate or compositions are combined in a mixture with a pharmaceutically suitable excipient. Sterile phosphate-buffered saline is one example of a pharmaceutically suitable excipient. Other suitable excipients are well known to those in the art. (See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or compositions disclosed herein can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic or diagnostic conjugate or naked antibody. Control release preparations can be prepared through the use of polymers to complex or adsorb the immunoconjugate or naked antibody. For example, biocompatible polymers include matrices of poly(ethylene-co-vinyl acetate) and matrices of a polyanhydride copolymer of a stearic acid dimer and sebacic acid. Sherwood et al., Bio/Technology 10: 1446 (1992). The rate of release of an immunoconjugate or antibody from such a matrix depends upon the molecular weight of the immunoconjugate or antibody, the amount of immunoconjugate or antibody within the matrix, and the size of dispersed particles. Saltzman et al., Biophys. J. 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or compositions may also be administered to a mammal subcutaneously or even by other parenteral routes. Moreover, the administration may be by continuous infusion or by single or multiple boluses. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of immunoconjugate or composition including the immunoconjugate that is in the range of from about 1 mg/kg to 20 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule.

For purposes of therapy, the immunoconjugate, or composition including the immunoconjugate, is administered to a mammal in a therapeutically effective amount. A suitable subject for the therapeutic and diagnostic methods disclosed herein is usually a human, although a non-human animal subject is also contemplated. An antibody preparation is said to be administered in a "therapeutically effective amount" if the amount administered is physiologically significant. An agent is physiologically significant if its presence results in a detectable change in the physiology of a recipient mammal. In particular, an antibody preparation is physiologically significant if its presence invokes an antitumor response or mitigates the signs and symptoms of an autoimmune disease state. A physiologically significant effect could also be the evocation of a humoral and/or cellular immune response in the recipient mammal.

Chronic Lymphocytic Leukemia

In a preferred embodiment, the compositions or immunoconjugates described herein are of use for therapy of chronic lymphocytic leukemia (CLL). CLL is a presently incurable progressive disease for which new therapies are required. Therapy with monoclonal antibodies (mAb) has improved the outcome of patients with CLL, making further investigation of novel antibodies directed against alternative and specific targets on B cells an important area of research.

CLL is the most common adult leukemia, and is a progressive and incurable disease. Present CLL treatments include alkylating chemotherapeutic drugs (e.g., chlorambucil and cyclophosphamide), purine analogs (e.g., fludarabine), and most recently monoclonal antibodies (mAb). Antibodies such as rituximab that target the CD20 antigen selectively expressed on CLL cells augment the cytotoxicity of traditional chemotherapy agents, and are associated with improved response rates and progression-free survival (Robak et al., *ASH Annual Meeting Abstracts*. Nov. 16, 2008; 112(11):lba; Hallek et al., *ASH Annual Meeting Abstracts*. Nov. 16, 2008 2008; 112(11):325; Keating et al., *J Clin Oncol.* 2005, 23:4079-4088; Byrd et al., *Blood*, 2005, 105:

49-53). However, nearly all patients eventually relapse after such treatments, indicating a need for novel and specific therapeutic agents for CLL.

CD74 is a type II transmembrane protein expressed on B cells which has recently been pursued as a target for antibody mediated therapy (Stein et al., *Clin Cancer Res.* 2007, 13:5556s-5563s). It associates with the α and β chains of HLA-DR, and normally functions as an MHC class II chaperone. However, signaling through CD74 is also implicated in B-cell proliferation, NF-κB activation, and cell survival (Binsky et al., *Proc Natl Acad Sci USA.* 2007, 104:13408-13413; Starlets et al., *Blood,* 2006, 107:4807-4816). CD74 expression is increased on the surface of leukemic B cells, making it an attractive target for CLL and other B-cell malignancies. CD74 signaling is initiated following engagement with macrophage migration-inhibitory factor (MIF), and subsequent activation of survival pathways to inhibit apoptosis and stimulate proliferation (Gore et al., *J Biol Chem,* 2008, 283: 2784-2792; Leng et al., *J Exp Med,* 03, 7:1467-1476). Additionally, a recent study demonstrates that CD74 signaling induces Tap63 and VLA-3 to enhance CLL cell survival and homing to the bone marrow (Binsky et al., *J Immunol* Mar. 31, 2010 epub). Therefore, disruption of CD74 signaling represents a potential therapeutic option in CLL and other CD74-expressing malignancies (Stein et al., *Clin Cancer Res,* 2007, 13:5556s-5563s).

Described herein is an antagonistic humanized antibody to CD74, milatuzumab (hLL1). Milatuzumab has demonstrated anti-proliferative activity in non-Hodgkin lymphoma (NHL) and multiple myeloma (MM) cell lines and extended the survival of SCID mice injected with NHL and MM cells (Stein et al., *Clin Cancer Res,* 2007, 13:5556s-5563s; Starlets et al., *Blood,* 2006, 107:4807-4816; Griffiths et al., *Clin Cancer Res,* 2003, 9:6567-6571). However, little is known about the effect of milatuzumab in CLL. The Examples below demonstrate that milatuzumab mediates direct cytotoxicity in CLL cells by a mechanism involving aggregation of CD74 on the cell surface. Furthermore, incorporation of milatuzumab into a liposome potentiates the cytotoxic effect of this antibody, suggesting a novel therapeutic formulation.

Methods of Treatment

Contemplated herein is the use of immunoconjugates or compositions including immunoconjugates for treatment of a CD74 expressing disease. The disease or disorder may be selected from the group consisting of cancer, neoplasia, an immune dysregulation disease, an autoimmune disease, organ graft rejection, and graft versus host disease. The CD74 expressing disease may be selected from the group consisting of a solid tumor, non-Hodgkin's lymphoma, Hodgkin's lymphoma, multiple myeloma, a B-cell disease and/or a T-cell disease. The solid tumor may be selected from the group consisting of a melanoma, carcinoma and sarcoma. The carcinoma may be selected from the group consisting of a renal carcinoma, lung carcinoma, intestinal carcinoma and stomach carcinoma. The B-cell disease may be selected from the group consisting of indolent forms of B-cell lymphomas, aggressive forms of B-cell lymphomas, chronic lymphatic leukemias, acute lymphatic leukemias, multiple myeloma, B-cell disorders and other diseases. In particular, the compositions described herein are particularly useful for treatment of various autoimmune as well as indolent forms of B-cell lymphomas, aggressive forms of B-cell lymphomas, chronic lymphatic leukemias, acute lymphatic leukemias, multiple myeloma, and Waldenstrom's macroglobulinemia. For example, humanized anti-CD74 antibody components and immunoconjugates can be used to treat both indolent and aggressive forms of non-Hodgkin's lymphoma.

More specifically, the method for treating a B-cell disease may include administering to a subject with a B-cell related disease, a therapeutic composition comprising an immunoconjugate including an anti-CD74 binding molecule, (e.g., a humanized, chimeric, or human anti-CD74 antibody or fragment thereof or antibody fusion protein thereof), a pharmaceutically acceptable carrier, and optionally a therapeutic agent, wherein the B-cell disease is a lymphoma or leukemia. More specifically, the B-cell disease may be selected from indolent forms of B-cell lymphomas, aggressive forms of B-cell lymphomas, multiple myeloma, chronic lymphatic leukemias, or acute lymphatic leukemias. The immunoconjugate or composition comprising the immunoconjugate may be administered intravenously, intramuscularly or subcutaneously at a dose of 20-2000 mg. The method may further comprise administering the immunoconjugate or composition before, simultaneously with, or after the administration of at least one additional therapeutic agent or diagnostic agent used to treat the B-cell disease. The additional agent may include an additional immunoconjugate as described herein, including a therapeutic or diagnostic agent. A therapeutic agent may be selected from the group consisting of a naked antibody, an immunomodulator, a hormone, a cytotoxic agent, an enzyme, and/or an antibody conjugated to at least one immunomodulator, radioactive label, hormone, enzyme, or cytotoxic agent, or a combination thereof. The immunomodulator preferably is a cytokine and the cytotoxic agent preferably is a drug or toxin. The antibody that is administered in combination as a naked antibody or as a supplemental immunoconjugate preferably is reactive with an antigen selected from the group consisting of carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM-6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-IA, MIP-1B, MIF, MUC1, MUC2, MUC3, MUC4, MUC5, PAM4 antigen, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5, and an oncogene product.

Also contemplated herein is the treatment of a disease comprising administering to a subject with a CD74 antigen-positive disease other than lymphoma or leukemia, a therapeutic composition that includes: (1) an immunoconjugate of an anti-CD74 binding molecule and a liposome; (2) optionally, an effector moiety; and (3) a pharmaceutically acceptable excipient. The immunoconjugate or composition may be administered intravenously, intramuscularly or subcutaneously at a dose of 20-5000 mg. Further, the immunoconjugate may be administered before, simultaneously with, or after the administration of at least one additional therapeutic agent or diagnostic agent. Therapeutic agents, as described above and throughout the specification, may include an immunomodulator, a hormone, a cytotoxic agent, or a binding molecule (either naked or conjugated to at least one immunomodulator, radioactive label, enzyme, hormone, cytotoxic agent, antisense oligonucleotide, or a combination thereof, where the immunomodulator preferably is a cytokine and the cytotoxic agent preferably is a drug or toxin). A therapeutic agent or diagnostic agent may include the compositions or immunoconjugates as disclosed herein. When an antibody is administered in combination with the therapeutic and/or diagnostic composition to treat a malignancy that is not a B-cell malignancy, it should be reactive with a tumor marker other than CD74, which is expressed by the cells that comprise the malignancy that is treated, and the antibody should be formulated in a pharmaceutically acceptable vehicle. Examples of antibodies that can be administered for malignant melanoma associated antigens are those antibodies reactive with MART-1, TRP-1, TRP-2 and gp100. Further, preferred antibodies to multiple myeloma-associated antigens are those reactive with MUC1 and CD38.

The compositions for treatment contain at least one immunoconjugate, which typically includes a humanized, chimeric or human monoclonal anti-CD74 antibody alone or in combination with other antibodies, such as other humanized, chimeric, or human antibodies. In particular, combination therapy wherein the immunoconjugate includes a fully human antibody is also contemplated.

The compositions also may include an immunomodulator as an effector. As used herein, the term "immunomodulator" includes may be selected from a cytokine, a stem cell growth factor, a lymphotoxin, an hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-$\alpha$, -$\beta$ or -$\gamma$, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\beta$; platelet-growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); interleukins (ILs) such as IL-1, IL-1$\alpha$, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines. The immunomodulator may be present in the composition, or alternatively, the immunomodulator can be administered before, simultaneously with, or after administration of the therapeutic and/or diagnostic compositions. As discussed supra, the anti-CD74 antibody may also be conjugated to the immunomodulator. The immunomodulator may also be conjugated to a hybrid antibody consisting of one or more antibodies binding to different antigens.

Multimodal therapies contemplated herein further include immunotherapy with immunoconjugates that include anti-CD74 binding molecules supplemented with administration of additional binding molecules, (e.g., anti-CD22, anti-CD19, anti-CD21, anti-CD20, anti-CD80, anti-CD23, anti-CD46 or HLA-DR, preferably the mature HLA-DR dimer antibodies in the form of naked antibodies, fusion proteins, or as immunoconjugates). Further, a liposome as described herein, may include binding molecules in addition to anti-CD74 binding molecules. Useful antibodies may be polyclonal, monoclonal, chimeric, human or humanized antibodies that recognize at least one epitope on the above-noted antigenic determinants. For example, anti-CD19 and anti-CD22 antibodies are known to those of skill in the art. (See, e.g., Ghetie et al., Cancer Res. 48:2610 (1988); Hekman et al., Cancer Immunol. Immunother. 32:364 (1991); Longo, Curr. Opin. Oncol. 8:353 (1996) and U.S. Pat. Nos. 5,798,554 and 6,187,287.)

In another form of multimodal therapy, subjects receive anti-CD74 immunoconjugates, in conjunction with standard cancer chemotherapy. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., Eur. J. Haematol. 51: 18 (1993). Other suitable combination chemotherapeutic regimens are well known to those of skill in the art. (See, e.g., Freedman et al., "Non-Hodgkin's Lymphomas," in CANCER MEDICINE, VOLUME 2, 3rd Edition, Holland et al. (eds.), pages 2028-2068 (Lea & Febiger 1993)). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second-generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and bryostatin-1. In a preferred multimodal therapy, both chemotherapeutic drugs and cytokines are co-administered with an antibody, immunoconjugate or fusion protein. The cytokines, chemotherapeutic drugs and antibody or immunoconjugate can be administered in any order, or together.

In a preferred embodiment, NHL is treated with 4 weekly infusions of a humanized anti-CD74 immunoconjugate (e.g., a therapeutic emulsion) at a dose of 200-400 mg/m$^2$ weekly for 4 consecutive weeks or every-other week (iv over 2-8 hours), repeated as needed over next months/yrs. Also preferred, NHL is treated with 4 semi-monthly infusions as above, but combined with epratuzumab (anti-CD22 humanized antibody) on the same days, at a dose of 360 mg/m$^2$, given as an iv infusion over 1 hour, either before, during or after the anti-CD74 immunoconjugate infusion. Still preferred, NHL is treated with 4 weekly infusions of the anti-CD74 immunoconjugate as above, combined with one or more injections of CD22 antibody radiolabeled with a therapeutic isotope such as yttrium-90 (at dose of $^{90}$Y between 5 and 35 mCi/meter-square) as one or more injections over a period of weeks or months.

In addition, a therapeutic composition as contemplated herein can contain a mixture or hybrid molecules of monoclonal anti-CD74 immunoconjugates directed to different, non-blocking CD74 epitopes. Accordingly, contemplated herein are therapeutic compositions comprising a mixture of monoclonal anti-CD74 immunoconjugates that bind at least two CD74 epitopes. Additionally, the immunoconjugates described herein may contain a mixture of anti-CD74 antibodies with varying CDR sequences.

As discussed supra, the immunoconjugates can be used for treating B cell lymphoma and leukemia, and other B cell diseases or disorders as well as other malignancies in which affected or associated malignant cells are reactive with CD74. For example, anti-CD74 immunoconjugates can be used to treat immune dysregulation disease and related autoimmune diseases, including Class-III autoimmune diseases such as immune-mediated thrombocytopenias, such as acute idiopathic thrombocytopenic purpura and chronic idiopathic thrombocytopenic purpura, dermatomyositis, Sjogren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

In particular, immunoconjugates including humanized, chimeric or human anti-CD74 antibodies or fragments thereof or antibody fusion proteins thereof are administered to a subject with one or more of these autoimmune diseases. The anti-CD74 immunoconjugates disclosed herein are particularly useful in the method of treating autoimmune disorders, disclosed in U.S. Pat. No. 7,074,403, the Figures and Examples section of which is incorporated herein by reference. Preferably the anti-CD74 immunoconjugate is administered intravenously, intramuscularly or subcutaneously at a dose of 20-5000 mg. Further, the anti-CD74 immunoconjugate may be administered before, during or after the administration of at least one therapeutic agent or diagnostic agent. The therapeutic agent, as described above and throughout the specification, may include an antibody, an immunomodulator, a hormone, an enzyme, a cytotoxic agent, an antibody conjugated to at least one immunomodulator, radioactive label, hormone, enzyme, or cytotoxic agent, antisense oligonucleotide or a combination thereof, where the immunomodulator may be a cytokine and said cytotoxic agent may be a drug or toxin. The therapeutic agent may include an immunoconjugate as described herein. Antibodies that may be administered in combination as a naked antibody or as a supplemental immunoconjugate include antibodies that react with carbonic anhydrase IX, B7, CCCL19, CCCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM-6, alpha-fetoprotein (AFP), VEGF (e.g. AVASTIN®, fibronectin splice variant), ED-B fibronectin (e.g., L19), EGP-1, EGP-2 (e.g., 17-1A), EGF receptor (ErbB1) (e.g., ERBITUX®), ErbB2, ErbB3, Factor H, FHL-1, Flt-3, folate receptor, Ga 733, GROB, HMGB-1, hypoxia inducible factor (HIF), HM 1.24, HER-2/neu, insulin-like growth factor (ILGF), IFN-γ, IFN-α, IFN-β, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5, placental growth factor (PlGF), PSA (prostate-specific antigen), PSMA, pancreatic cancer mucin, PAM4 antigen, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), VEGFR, RANTES, T101, as well as cancer stem cell antigens, complement factors C3, C3a, C3b, C5a, C5, an oncogene product and mature HLA-DR, preferably a mature HLA-DR dimer, formulated in a pharmaceutically acceptable vehicle.

Method of Diagnosis

Also provided is a method of diagnosing a disease in a subject, diagnosed with or suspected of having at least one of the diseases selected from the groups consisting of lymphoma, leukemia, myeloma, other CD74-expressing malignancies, immune dysregulation disease, autoimmune disease and a combination thereof, comprising administering to said subject a diagnostically effective amount of a composition that includes (1) an immunoconjugate including at least one anti-CD74 binding molecule conjugated to a liposome, (2) a diagnostic agent, and (3) a pharmaceutically acceptable excipient. The diagnostic agent may be covalently, non-covalently, or otherwise associated with one or more components of the composition. A useful diagnostic agent may include a radioisotope, wherein the photons of the radioisotope are detected by radioscintigraphy or PET, or a metal that can be detected by MRI, or a liposome or gas filled liposome, and wherein the liposome can be detected by an ultrasound scanning device. As such, the immunoconjugate may form a liposome, and/or the diagnostic agent may comprise a second liposome.

The internalization of the immunoconjugate into target cells can be followed by fluorescence labeling, essentially according to the procedure of Pirker et al., J. Clin. Invest., 76: 1261 (1985). Further, a method for screening/diagnosing bone cancers as described in Juweid et al., 1999, could benefit from the immunoconjugates disclosed herein. Accordingly, a method comprising $^{99m}$Tc-labeled humanized or chimeric anti-CD74 antibody immunoconjugates is contemplated.

EXAMPLES

Example 1

Preparation of Anti-CD74 Immunoliposomes Carrying FUdR-dO

Triolein (TO), egg phosphatidylcholine (EPC), dipalmitoyl phosphatidylethanolamine (DPPE), cholesterol (CHOL), 8-hydroxy-1,3,6-pyrenetrisulfonate (HPTS), polyoxyethylenesorbitan monooleate (sorbitan 80), methoxypolyethyleneglycol (mean mol. wt 2000), oleoyl chloride, 3-(4,5-dimethylthiazol-2-yl)-2,5-diphenyltetrazolium bromide (MTT) and DL-dithiotreitol (DTT) were obtained from Sigma Chemical Co. (St. Louis, Mo.). Poly(ethylene glycol)-maleimide-N-hydroxy-1-succinimidyl ester (MAL-PEG$_{2000}$-NHS) was purchased from Shearwater Polymers Europe (Enschede, The Netherlands). [$^3$H]Cholesteryl oleoyl ether (COE) and [$^{14}$C]dipalmitoyl phosphatidylcholine were obtained from Amersham International plc (Amersham, UK). A $PEG_{2000}$ derivative of DPPE with a maleimide group at the distal terminus of the PEG chain (DPPE-PEG-MAL) was synthesized by reacting 25 µmol NHS-PEG-MAL with 23 µmol DPPE and 50 µmol triethylamine in chloroform for 6 h at 40° C. The product was purified by preparative silica gel TLC. 3',5'-O-dioleoyl-FUdR (FUdR-dO) was synthesized by adding 20 µmol oleoyl chloride and 50 µl N,N-diisopropylethylamine to 10 µmol FUdR in dimethylacetamide. The mixture was incubated overnight at 40° C. and then water was added to the mixture and the fatty acid derivative of FUdR was extracted with chloroform. The prodrug was purified by preparative silica gel TLC with chloroform/methanol (95:5) as eluent.

The Burkitt's lymphoma cell lines, Raji and Ramos, Jurkat acute lymphoblastic leukemia T-cells and HL-60 myelomonocytic leukemia cells, obtained from American Type Culture Collection (Rockville, Md.), were grown in RPMI 1640 medium with 10% heat-inactivated fetal calf serum. Cells were maintained at 37° C. and gassed with 5% $CO_2$ in air.

The anti-CD74 Ab, LL1, was obtained from Immunomedics, Inc. (Morris Plains, N.J.). It was labeled with fluorescein (FITC) for quantitation.

Submicron lipid emulsions were prepared as described in detail elsewhere. (See, Lundberg, J. Pharm. Sci., 83:72-75 (1994); Lundberg et al., Int. J. Pharm., 134:119-127 (1996)). The composition of the drug-loaded emulsions was TO, EPC, polysorbate 80, DPPE-$PEG_{2000}$-MAL, FUdR-dO 2:2:0.8:0.6:0.3 (w/w). The components were dispensed into vials from stock solutions and the solvent was evaporated to dryness under reduced pressure. Phosphate-buffered saline (PBS) was added and the mixture was heated to 50° C., vortex mixed for 30 s, and sonicated with a Branson probe sonicator for 2 min.

Drug loaded liposomes were composed of EPC, DPPE-$PEG_{2000}$-MAL, FUdR-dO 1:0.2:0.1 (w/w). In experiments involving HPTS-encapsulated liposomes the composition was EPC, CHOL, DPPE-PEG2000-MAL 2:0.5:0.4. When required, the lipids were labeled with trace amounts of $[^3H]$ COE. Dried lipid films were hydrated in 25 mM HEPES and 140 mM NaCl buffer (pH 7.4), (containing 35 mM HPTS when appropriate) subjected to five freezing-thawing cycles and subsequent sonication for 2 min with a Branson probe sonicator. The phospholipid concentration was quantitated by $[^{14}C]$DPPC. MAL 2:0.5:0.4. Coupling of LL1 to liposomes was performed by reaction between the maleimide (MAL) groups at the distal PEG termini on the surface of the liposomes and free thiol groups on the Ab. Before the coupling reaction LL1 was reduced with 50 mM dithiotreitol for 1 h at 4° C. in 0.2 M tris buffer (pH6.5). The reduced Ab was separated from excess dithiotreitol by use of Sephadex G-25 spin-columns, equilibrated with 50 mM sodium acetate buffered 0.9% saline (pH 5.3). The conjugation was performed in HEPES-buffered saline (pH 7.4) for 16 h at room temperature under argon. Excess maleimide groups were blocked with 2 mM 2-mercaptoethanol for 30 min, whereafter excess Ab and 2-mercaptoethanol were removed on a Sepharose CL-4B column. The immunoliposomes were collected near the void volume of the column, passed through a 0.22 µm sterile filter and stored at 4° C. The coupling efficiency was estimated by use of fluorescein labeled LL1.

Example 2

Cellular Uptake and Metabolism of the Anti-CD74 Immunoliposomes

Liposomes containing the non-exchangeable marker $[^3H]$ COE were used to study the cellular uptake of drug carrier. After completed incubation, the cells were thoroughly washed three times with cold PBS and the radioactivity measured by liquid-scintillation counting. The pH-sensitive probe HPTS was used to study the internalization of liposomes to low pH compartments. HPTS exhibits two major fluorescence excitation maxima: a peak at 403 maximal at low pH values and a peak at 454 maximal at high pH values, while the fluorescence is independent of pH at 413 nm (isobestic point). (See, Straubinger, et al., Biochemistry, 29:4929-4939 (1990)). The ratio between the fluorescence at 454 nm and 413 nm can be used to study the internalization of the HPTS-liposomes to intracellular acidic compartments. HPTS-liposomes were diluted to 80 µM phospholipid in HEPES buffer and added to culture dishes ($4 \times 10^6$ cells) at 37° C. After incubation for 6 h the cells were washed twice with cold PBS and the fluorescence was measured in a stirred cuvette at 20° C. Peak heights were measured at 510 nm emission at the two excitation wavelengths (413 and 454 nm) and corrected for appropriate background fluorescence.

The concentration-dependent cellular association of liposomes with coupled LL1 and liposomes without coupled LL1 was examined (not shown). Association of liposomes with and without coupled LL1 was concentration dependent (not shown). The Burkitt's lymphoma cells, Raji, showed a massive interaction with LL1-liposome complexes as compared to untargeted preparations (not shown). LL1-emulsion conjugates, labeled with the nontransferable compound $[^3H]$ COE, were taken up about 50 times faster than unconjugated emulsions by Raji cells in culture (not shown). The fast and massive uptake of immunoemulsions is demonstrated by the fact that under standard incubation conditions about 30% of the added preparation was associated with cells after 24 h (not shown). The corresponding association of emulsions without coupled Ab was about 0.6% (not shown). The uptake values for Ramos cells were considerably lower but still about 30 times higher for LL1-complexes than for uncomplexed emulsions (not shown). The time-dependent association of targeted liposomes was fairly linear up to 24-h, but at prolonged incubation times the curve declined (not shown).

Example 3

Specificity of Immunoconjugates

The cell specificity of the preparations was tested on HL-60 and Jurkat cells. The cellular association obtained after 24 h was between 1 and 2% for both cell types with no evident difference between conjugates and plain emulsions (not shown). This extent of cellular association clearly represent unspecific uptake. The specificity of the interaction was further studied by measuring the cellular association of $[^3H]$ COE-labeled LL1-emulsions versus the amount of LL1 per emulsion EPC (not shown). These experiments demonstrated that association of the LL1-emulsions was dependent on the concentration of LL1 (not shown). The specificity of the interaction of immunoemulsions with cells was also studied by displacement experiments. Free LL I competed effectively with the LL 1-emulsion complexes and at high concentrations the cellular association was practically abolished (not shown). These findings strongly indicate that LL1 preserves its immunoreactivity after binding to liposomes.

Example 4

Endocytosis of HPTS-Containing Immunoliposomes

The intracellular fate of LL1-liposomal complexes was studied by use of the pH-sensitive probe HPTS. The spectral shifts of the probe with changes in pH make it a useful marker of the uptake and fate of the encapsulated dye. Internalization of LL1-liposomes to low-pH compartments was demonstrated by the fluorescence ratio $\lambda_{ex}$ 454/413. Values near 0.6 were obtained which corresponds to a pH value of 6.5 (not shown). This value is near those obtained by other authors with HPTS-immunoliposomes. See Kirpotin, et al., Biochemistry 36 (1997) 66-75; Lopes de Menezes, et al., J. Liposome Res. 9 (1999) 199-228. HPTS-liposomes without ligand gave values near 0.8, which corresponds to a pH value of about 7.0. See Lundberg, et al., Int. J. Pharm. 205 (2000) 101-108. It thus seems very likely that the LL1-drug-liposome complexes are delivered to and catabolized by the lysosomes.

Example 5

Cytotoxicity Assays

Comparison of the in vitro cytotoxicity of free FUdR and FUdR-dO-loaded emulsions and liposomes with and without coupled LL1 was performed on Raji human B-cell lymphoma lines with a proliferation assay utilizing tetrazolium dye, MTT. (See, Mosmann, J. Immun. Meth., 65:55-63 (1983)). To begin, $4\times10^5$ cells were plated in 24-well plates and incubated with drug containing preparations. Control experiments included free LL1 and drug free emulsions and liposomes. Cells were incubated for 24 h at 37° C. in an atmosphere of 95% humidity and 5% $CO_2$. At the 24 h time point, the cells were washed twice before replacing with fresh media and incubated for an additional 48 h. At the end of the incubation time, tetrazolium dye was added, the formed reduction product was spun down, dissolved in EtOH:DMSO 1:1 and read at 570 nm.

The cytotoxic activity of FUdR-dO in LL1 conjugated emulsions and liposomes was tested and compared with the activity of unconjugated drug-liposomes on Raji lymphoma cells (not shown). The effect of free FUdR (in PBS) was also recorded. The cells were incubated with the various preparations for 24-h, followed by an additional 48-h in fresh medium. From the dose-response curves it could be seen that FUdR-dO is somewhat more efficacious in emulsions than in liposomes (not shown). However, the activity of FUdR-dO administered in both LL1-emulsions and LL1-liposomes exceeded that of FUdR (not shown). The IC70 values obtained were 0.45, 1.25, 5.3 and 7.3 µM for FUdR-dO loaded LL1-emulsions, LL1-liposomes, emulsions and liposomes, respectively. The corresponding value for FUdR was calculated to 4.35 µM. The $IC_{50}$ values were 2.5, 5.3 and 7.0 µM for LL1-emulsions, LL1-liposomes and FudR, respectively (FUdR-dO in plain emulsions and liposomes did not reach that level (not shown).

The prodrug FUdR-dO employed in this study shows several advantageous features for administration in liposomes. It is amphiphilic and will be situated in the phospholipid monolayer and bilayer of lipid emulsions and liposomes, respectively. This makes the preparation of drug-liposome very convenient; the components are just mixed together and sonicated. An alternative method, which is more suited for large scale production, would be the use of high pressure homogenization.

A prerequisite for site-specific delivery of the prodrug to the target cells is the stable entrapment of the prodrug in the drug-liposome. The unspecific transfer of FUdR-dO from liposome to cells was not actually measured but the much higher cytotoxic activity of the LL1-conjugated preparations indicated that unspecific transfer of prodrug to cells is relatively low (not shown). That some degree of surface transfer probably occurs finds support by a study of Koning et al., Biochim. Biophys. Acta 1420 (1999) 153-167. They found that dipalmitoyl-FUdR immunoliposomes, without internalization, could deliver the prodrug to target cells more efficient than liposomes without antibody.

The prodrug concept comprises a pharmacologically inactive compound that is activated when exposed into the target cells. In this respect FUdR-dO may fulfill the criteria of a good prodrug. It has been shown that FUdR fatty acid esters are hydrolyzed fast in cells, apparently in lysosomes. See id. An efficient intracellular liberation of the parent drug FUdR is also indirectly supported by the high cytotoxic efficacy of the FUdR-dO preparations.

This in vitro study demonstrates the potential for site-specific delivery of anti-cancer drugs by use of liposomes with LL1 as targeting ligand. Several recent studies also show that liposomes, even without attached ligand, can give in vivo advantage as administration vehicles for lipophilic and amphiphilic drugs. See Constantinides et al., Pharm. Res. 17 (2000) 175-182; Perkins et al., Int. J. Pharm. 200 (2000) 27-39; Born et al., J. Controlled Release 74 (2001) 325-333; and Maranhao et al., Cancer. Chemother. Pharmacol. 49 (2002) 487-498.

An explanation for such a favorable effect appears to be that the half-life of the drug increases and the tolerability is improved so that high doses can be administered. A recent in vivo study with nude mice demonstrated specific Ab localization of LL1 to Ramos xenografts. See Shih et al., Cancer Immunol. Immunother. 49 (2000) 208-216. The present study shows an improved cytotoxic activity of the targeted prodrug compared to the parent drug. Immunoliposomes generally show lower or similar activity compared to the untargeted drug, but still demonstrate improved efficacy in in vivo experiments. See Moase et al., Biochim. Biophys. Acta 1510 (2001) 43-55; Lopes de Menezes et al., Cancer Res. 58 (1998) 3320-3330.

Example 6

Therapy of Chronic Lymphocytic Leukemia

As disclosed herein, milatuzumab, a humanized antibody to CD74, used with an in vitro crosslinking antibody induced cytotoxicity in CLL cells in a caspase- and stromal-independent manner associated with aggregation of CD74 on the cell surface. Incorporation of milatuzumab into an immunoliposome induced even more of a cytotoxic response as in vitro crosslinking, representing a novel therapeutic formulation for this antibody. These results demonstrate the feasibility of using milatuzumab-immunoliposome as a therapeutic agent for CLL.

Materials and Methods

Patients, cell separation, culture conditions, and reagents. For in vitro studies, written, informed consent was obtained to procure cells from patients with previously diagnosed CLL, as defined by the modified NCI criteria (Cheson et al., *Blood*, 1996, 87:4990-4997). Isolated mononuclear cells were negatively B-cell selected and placed in culture, as previously described (Lucas et al., *Blood*, 2009, 113:4656-4666). HS-5 stromal cells were obtained from the ATCC. CD40L was purchased from Peprotech (Rocky Hill, N.J.). Milatuzumab was provided by Immunomedics, Inc. (Morris Plains, N.J.). Goat anti-human IgG antibody (Fc gamma fragment-specific, anti-Fc) was purchased from Jackson ImmunoResearch Laboratories (West Grove, Pa.). Q-VD-OPH pan-caspase inhibitor was purchased from MP Biomedicals (Solon, Ohio).

Flow cytometry assays. Viability was determined by flow cytometry using propidium iodide (PI). For surface staining, CLL cells were washed in PBS and stained with antibodies to CD20 or CD74 (BD Biosciences, San Jose, Calif.; anti-CD74 MAb-BD catalog #55540/clone M-B741).

Immunoblot analysis. Immunoblots of whole cell lysates were performed as described (Johnson et al., *Blood*, 2006, 108:1334-1338). Antibodies used included PARP (Calbiochem, Gibbstown, N.J.), caspase 3 and 9 (R&D Systems, Minneapolis, Minn.), and tubulin (Santa Cruz Biotechnology, Santa Cruz, Calif.).

Preparation of Immunoliposome (Il). Immunoliposomes (ILs) were Prepared as previously described (Sapra and Allen, *Cancer Res*, 2002, 62:7190-7194). A post-insertion method was used to incorporate milatuzumab into preformed liposomes, and targeted milatuzumab-IL were prepared with an antibody-to-lipid ratio of 1:1000. Lipids Chol:Egg-PC:PEG-DSPE (molar ratio=33.5:65:1.5) were dissolved in ethanol and a thin lipid layer was formed under ROTAVAPOR®. Lipids were rehydrated in PBS and particle size was reduced by high pressure extrusion with nuclear polycarbonate membranes (pore sizes 0.2 and 0.1 mm, Northern Lipids). Liposome size distribution was analyzed on a NICOMP® Particle Sizer Model 370 (Particle Sizing Systems, Santa Barbara, Calif.). Volume weighted analysis showed particle size of approximately 100 nm.

A post-insertion method was adopted to incorporate antibody (milatuzumab) into preformed liposomes. In this method, milatuzumab was reacted with 10× Traut's reagent in PBS (pH 8.0) for 2 hr at room temperature to yield sulhydryl modified antibodies. Separation of milatuzumab-SH from unreacted 2-iminothiolane was performed with a SEPHADEX® PD-10 desalting column eluted with PBS (pH 6.5). The milatuzumab-SH was added to Mal-PEG-DSPE at a ratio of 10:1 (Mal-PEG-DSPE:milatuzumab-SH), and coupled overnight at room temperature. This antibody mixture was then incubated with liposomes for 1 hr at 37° C. to form targeted ILP with antibody-to-lipid ratios of 1:1000. Non-coupled antibody was separated on a SEPHAROSE® CL-4B column using PBS (pH 7.4). All liposomal suspensions were filtered through 0.22 mM PES syringe filters to ensure sterility. Milatuzumab-ILP was stored at 4° C. until use.

Statistical analysis. All reported statistical evaluations were performed by the Center for Biostatistics at Ohio State University. Since the observations from the same patient are correlated, linear mixed effects models were used for analysis to take account of this within patient correlation. Treatment differences were estimated and tested from these models. The Holm's step-down procedure was used to adjust for multiple comparisons or multiple endpoints when necessary. P-values<0.05 for single comparisons or after adjustment for multiple comparisons were considered significant.

Results and Discussion

We first determined the in vitro survival of primary CLL cells after milatuzumab treatment. As shown in FIG. 5A and FIG. 5B, milatuzumab (mila) with anti-Fc crosslinker rapidly induced significant cell death compared to anti-Fc alone (difference of 18% averaged across time points, N=26, P<0.0001). This result was verified by MTT assay (not shown). This effect was dependent on crosslinking, since milatuzumab alone had no cytotoxic effect on the cells. Furthermore, the induction of apoptosis was significantly greater (P<0.0001) than that of rituximab, and the effect of mila+anti-Fc was greater than that of rituximab+anti-Fc. Milatuzumab-mediated killing appeared to be caspase-independent, since treatment does not increase cleavage of caspases 3, 6, 8 or 9 or the caspase substitute PARP relative to Fc crosslinker control, although processing of caspase 2 was observed (FIG. 5C). While the pan-caspase inhibitor Q-VD-OPH is able to block cleavage of both PARP and caspase 2, it had no significant effect on milatuzumab-induced cell death (FIG. 5D; N+5; P=0.03).

The role of microenvironmental factors in the survival and drug resistance of CLL cells is becoming increasingly studied (Kurtova et al., *Blood*, 2009, 114:4441-50). The effect of milatuzumab was not significantly diminished by co-culture with a stromal cell line (FIG. 5E (panel i); 37.3% more cell death with mila+anti-Fc vs. anti-Fc alone in the absence of HS-5; 48.5% more cell death with mila+anti-Fc vs. anti-Fc alone in the presence of HS-5; N=11; P=0.10). In contrast, fludarabine-induced cytotoxicity was noticeably diminished by co-culture with stroma despite the variation in fludarabine responsiveness among individual samples (FIG. 5E (panel ii); 19.3% more cell death with fludarabine vs. vehicle control in the absence of HS-5; 2.2% more cell death with fludarabine vs. vehicle control in the presence of HS-5). Furthermore, treatment with CD40L, commonly found to protect CLL cells from cell death, was unable to prevent milatuzumab-induced cytotoxicity (FIG. 5E (panel iii); 23% more cell death with mila+anti-Fc vs. anti-Fc alone in the absence of CD40L; 29% more cell death with mila+anti-Fc vs. anti-Fc alone in the presence of CD40L; N=17; P=0.09N=17; P=0.11). Together, these data indicate that milatuzumab may be effective in vivo despite the presence of an intact microenvironment.

We next investigated whether milatuzumab was able to mediate antibody-dependant cellular cytotoxicity (ADCC). Similar to other reports in lymphoma cell lines (Stein et al., *Blood*, 2004, 104:3705-3711), no ADCC was detected with either mononuclear cells or granulocytes at any effector to CLL target cell ratio (data not shown). These findings indicate that direct apoptosis via CD74 ligation is likely the principal contributor to milatuzumab efficacy.

We next sought to determine how CD74 ligation by milatuzumab promoted cell death. We observed that upon milatuzumab treatment in the presence of crosslinking, CLL cells aggregated in culture (not shown) and the mean fluorescent intensity (MFI) of CD74 on the cell surface increased significantly (FIGS. 6A and 6B left; 1.50 vs. 5.03 MFI (anti-Fc vs. mile $_+$anti-Fe); N=14; P=0.0003). No significant change in surface expression of CD74 was observed following treatment with anti-Fc alone, while milatuzumab alone led to a slight decrease in surface CD74, potentially due to increased receptor internalization in the absence of crosslinker. In addition, significant surface retention of CD20 was not observed following in vitro crosslinking with milatuzumab (FIG. 6B, right; 6.36 vs. 5.56 MFI (anti-Fc vs. mila+anti-Fc) N=14; P=0.14), indicating that the increased surface CD74 is antigen-specific and not due to nonspecific antibody trapping between clustered cells. These data suggest that milatuzumab promotes the maintenance and/or accumulation of CD74 on the cell surface, which likely initiates downstream signaling pathway(s) leading to cell death. The lack of this effect following treatment with milatuzumab alone indicates that crosslinking is necessary for milatuzumab-induced cell death. However, association with Fc receptors on other cells in the microenvironment may not be sufficient to mediate this effect, as indicated by the lack of ADCC with milatuzumab (Stein et al., *Blood*, 2004, 104:3705-11). We therefore investigated whether other methods to promote receptor accumulation with milatuzumab induce a similar in vitro cytotoxic effect as crosslinking antibody.

Similar to previous studies with the anti-CD22 mAb, epratuzumab (Carnahan et al., *Mol Immunol*, 2007, 44:1331-41), we found that milatuzumab immobilized on a plastic cell culture plate increased cell death compared to the non-immobilized antibody, but this was not as active in cell killing compared to using soluble anti-Fc (data not shown; 18.2% vs. 43.2% PI positive, immobilized mila vs. mila+anti-Fc averaged across time points; N=6; P<0.0001). These results suggest that association of multiple receptors may be required to initiate a death signal, which is limited when antibodies are fixed on cell culture plates. Enhanced cell death through Fas signaling has been described for CD44 (Mielgo et al., *Apoptosis,* 2007, 12:2051-61), a binding partner for CD74, and is a suggested mechanism for milatuzumab (Berkova et al., *Expert Opin Investig Drugs,* 2010, 19:141-49).

Incorporation of internalizing antibodies into liposome particles has been described as a method for targeted drug delivery in B-cell malignancies (Sapra et al., *Cancer Res,* 2002, 62:7190-7194; *Clin Cancer Res,* 2005, 11:5257-5264). We found that incorporation of milatuzumab into a liposome (mila-IL) was able to mediate the same receptor aggregation on the cell surface as milatuzumab with anti-Fc (FIG. 6C), an effect which was not evident with liposome alone (mila-IL vs. liposome; 4.23 vs. 1.39 MFI; N=4; P=0.0003). Furthermore, mila-IL induced significantly 6 more cell death in CLL cells compared to IgG incorporated liposomes (FIG. 6D; mila-IL vs. IgG-IL; 36% vs. 4.8% PI positive; N=11; P<0.0001). Cell death induced by mila-IL was significantly higher than that caused by milatuzumab plus crosslinking in vitro (FIG. 6D; mila-IL vs. mila+anti-Fc; 36% vs. 25.5% PI positive; N=11; P=0.0003). This cytotoxicity was evident even without packaging the immunoliposome with a chemotherapeutic drug, such as doxorubicin, which has been described previously with this antibody (Sapra et al., *Clin Cancer Res,* 2005, 11:5257-5264).

Here, we provide evidence that the incorporation of milatuzumab into a liposome may induce cell death without the dependence on other cell types in the microenvironment. Together, these support the clinical application of mila-IL-based therapy in CLL and other CD74-positive malignancies.

All patents and other references cited in the specification are indicative of the level of skill of those skilled in the art to which the invention pertains, and are incorporated herein by reference, including any Tables and Figures, to the same extent as if each reference had been incorporated by reference individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the invention.

It will be readily apparent to one skilled in the art that varying substitutions and modifications may be made to the invention disclosed herein without departing from the scope and spirit of the invention. Thus, such additional embodiments are within the scope of the present invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

SEQUENCE LISTING

<160> NUMBER OF SEQ ID NOS: 20

<210> SEQ ID NO 1
<211> LENGTH: 16
<212> TYPE: PRT
<213> ORGANISM: Mus sp.

<400> SEQUENCE: 1

Arg Ser Ser Gln Ser Leu Val His Arg Asn Gly Asn Thr Tyr Leu His
1               5                   10                  15

<210> SEQ ID NO 2
<211> LENGTH: 7
<212> TYPE: PRT
<213> ORGANISM: Mus sp.

<400> SEQUENCE: 2

Thr Val Ser Asn Arg Phe Ser
1               5

<210> SEQ ID NO 3
<211> LENGTH: 9
<212> TYPE: PRT
<213> ORGANISM: Mus sp.

<400> SEQUENCE: 3

Ser Gln Ser Ser His Val Pro Pro Thr
1               5

<210> SEQ ID NO 4
<211> LENGTH: 5
<212> TYPE: PRT
<213> ORGANISM: Mus sp.

<400> SEQUENCE: 4

Asn Tyr Gly Val Asn
1               5

<210> SEQ ID NO 5
<211> LENGTH: 17
<212> TYPE: PRT
<213> ORGANISM: Mus sp.

<400> SEQUENCE: 5

Trp Ile Asn Pro Asn Thr Gly Glu Pro Thr Phe Asp Asp Asp Phe Lys
1               5                   10                  15

Gly

<210> SEQ ID NO 6
<211> LENGTH: 11
<212> TYPE: PRT
<213> ORGANISM: Mus sp.

<400> SEQUENCE: 6

Ser Arg Gly Lys Asn Glu Ala Trp Phe Ala Tyr
1               5                   10

<210> SEQ ID NO 7
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 7

```
cag atc cag ttg gtg cag tct gga cct gag ctg aag aag cct gga gag      48
Gln Ile Gln Leu Val Gln Ser Gly Pro Glu Leu Lys Lys Pro Gly Glu
1               5                   10                  15 aca gtc aag gtc acc tgc aag act tct gga tat acc ttc aca aac tat      96
Thr Val Lys Val Thr Cys Lys Thr Ser Gly Tyr Thr Phe Thr Asn Tyr
                20                  25                  30 gga gtg aac tgg ata aag cag act cca gga gag ggt tta cag tgg atg     144
Gly Val Asn Trp Ile Lys Gln Thr Pro Gly Glu Gly Leu Gln Trp Met
            35                  40                  45 ggc tgg ata aac ccc aac act gga gag cca aca ttt gat gat gac ttc     192
Gly Trp Ile Asn Pro Asn Thr Gly Glu Pro Thr Phe Asp Asp Asp Phe
        50                  55                  60 aag gga cga ttt gcc ttc tct ttg gaa tcc tct gcc agc act gcc ttt     240
Lys Gly Arg Phe Ala Phe Ser Leu Glu Ser Ser Ala Ser Thr Ala Phe
65                  70                  75                  80 ttg cag atc agc aac ctc aaa aat gag gac atg ggt aca tat ttc tgt     288
Leu Gln Ile Ser Asn Leu Lys Asn Glu Asp Met Gly Thr Tyr Phe Cys
```

```
                       85                   90                   95
tca aga tcg agg ggt aaa aac gaa gcc tgg ttt gct tat tgg ggc caa    336
Ser Arg Ser Arg Gly Lys Asn Glu Ala Trp Phe Ala Tyr Trp Gly Gln
            100                 105                 110 ggg act ctg gtc act gtc tct gaa                                    360
Gly Thr Leu Val Thr Val Ser Glu
        115                 120

<210> SEQ ID NO 8
<211> LENGTH: 120
<212> TYPE: PRT
<213> ORGANISM: Mus sp.

<400> SEQUENCE: 8

Gln Ile Gln Leu Val Gln Ser Gly Pro Glu Leu Lys Lys Pro Gly Glu
1               5                   10                  15

Thr Val Lys Val Thr Cys Lys Thr Ser Gly Tyr Thr Phe Thr Asn Tyr
            20                  25                  30

Gly Val Asn Trp Ile Lys Gln Thr Pro Gly Glu Gly Leu Gln Trp Met
        35                  40                  45

Gly Trp Ile Asn Pro Asn Thr Gly Glu Pro Thr Phe Asp Asp Asp Phe
    50                  55                  60

Lys Gly Arg Phe Ala Phe Ser Leu Glu Ser Ser Ala Ser Thr Ala Phe
65                  70                  75                  80

Leu Gln Ile Ser Asn Leu Lys Asn Glu Asp Met Gly Thr Tyr Phe Cys
                85                  90                  95

Ser Arg Ser Arg Gly Lys Asn Glu Ala Trp Phe Ala Tyr Trp Gly Gln
            100                 105                 110

Gly Thr Leu Val Thr Val Ser Glu
        115                 120

<210> SEQ ID NO 9
<211> LENGTH: 337
<212> TYPE: DNA
<213> ORGANISM: Mus sp.
<220> FEATURE:
<221> NAME/KEY: CDS
<222> LOCATION: (1)..(333)

<400> SEQUENCE: 9 gat gtt gtg atg acc caa act cca ctc tcc ctg cct gtc agt ctt gga    48
Asp Val Val Met Thr Gln Thr Pro Leu Ser Leu Pro Val Ser Leu Gly
1               5                   10                  15 gat caa gcc tcc atc tct tgc aga tct agt cag agc ctt gta cac aga    96
Asp Gln Ala Ser Ile Ser Cys Arg Ser Ser Gln Ser Leu Val His Arg
            20                  25                  30 aat gga aac acc tat tta cat tgg tac ctg cag aag cca ggc cag tct    144
Asn Gly Asn Thr Tyr Leu His Trp Tyr Leu Gln Lys Pro Gly Gln Ser
        35                  40                  45 cca aag ctc ctg atc tac aca gtt tcc aac cga ttt tct ggg gtc cca    192
Pro Lys Leu Leu Ile Tyr Thr Val Ser Asn Arg Phe Ser Gly Val Pro
    50                  55                  60 gac agg ttc agt ggc agt gga tca ggg aca gat ttc aca ctc aag atc    240
Asp Arg Phe Ser Gly Ser Gly Ser Gly Thr Asp Phe Thr Leu Lys Ile
65                  70                  75                  80 agt aga gtg gag gct gag gat ctg gga ctt tat ttc tgc tct caa agt    288
Ser Arg Val Glu Ala Glu Asp Leu Gly Leu Tyr Phe Cys Ser Gln Ser
                85                  90                  95 tca cat gtt cct ccc acg ttc ggt gct ggg acc aag ctg gag atc taac  337
Ser His Val Pro Pro Thr Phe Gly Ala Gly Thr Lys Leu Glu Ile
            100                 105                 110
```

<210> SEQ ID NO 10
<211> LENGTH: 111
<212> TYPE: PRT
<213> ORGANISM: Mus sp.

<400> SEQUENCE: 10

```
Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Ser His Val Pro Pro Thr Phe Gly Ala Gly Thr Lys Leu Glu Ile
            100                 105                 110
```

<210> SEQ ID NO 11
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 11

```
cag gtc caa ctg cag cag tct gga cct gag ctg aag aag cct gga gag    48
Gln Val Gln Leu Gln Gln Ser Gly Pro Glu Leu Lys Lys Pro Gly Glu
1               5                   10                  15 aca gtc aag gtc acc tgc aag act tct gga tat acc ttc aca aac tat    96
Thr Val Lys Val Thr Cys Lys Thr Ser Gly Tyr Thr Phe Thr Asn Tyr
            20                  25                  30 gga gtg aac tgg ata aag cag act cca gga gag ggt tta cag tgg atg   144
Gly Val Asn Trp Ile Lys Gln Thr Pro Gly Glu Gly Leu Gln Trp Met
        35                  40                  45 ggc tgg ata aac ccc aac act gga gag cca aca ttt gat gat gac ttc   192
Gly Trp Ile Asn Pro Asn Thr Gly Glu Pro Thr Phe Asp Asp Asp Phe
    50                  55                  60 aag gga cga ttt gcc ttc tct ttg gaa tcc tct gcc agc act gcc ttt   240
Lys Gly Arg Phe Ala Phe Ser Leu Glu Ser Ser Ala Ser Thr Ala Phe
65                  70                  75                  80 ttg cag atc agc aac ctc aaa aat gag gac atg ggt aca tat ttc tgt   288
Leu Gln Ile Ser Asn Leu Lys Asn Glu Asp Met Gly Thr Tyr Phe Cys
                85                  90                  95 tca aga tcg agg ggt aaa aac gaa gcc tgg ttt gct tat tgg ggc caa   336
Ser Arg Ser Arg Gly Lys Asn Glu Ala Trp Phe Ala Tyr Trp Gly Gln
            100                 105                 110 ggg act ctg gtc acc gtc tcc tca                                   360
Gly Thr Leu Val Thr Val Ser Ser
        115                 120
```

<210> SEQ ID NO 12
<211> LENGTH: 120
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Gln Ser Gly Pro Glu Leu Lys Lys Pro Gly Glu
1               5                   10                  15

Thr Val Lys Val Thr Cys Lys Thr Ser Gly Tyr Thr Phe Thr Asn Tyr
            20                  25                  30

Gly Val Asn Trp Ile Lys Gln Thr Pro Gly Glu Gly Leu Gln Trp Met
        35                  40                  45

Gly Trp Ile Asn Pro Asn Thr Gly Glu Pro Thr Phe Asp Asp Asp Phe
    50                  55                  60

Lys Gly Arg Phe Ala Phe Ser Leu Glu Ser Ser Ala Ser Thr Ala Phe
65                  70                  75                  80

Leu Gln Ile Ser Asn Leu Lys Asn Glu Asp Met Gly Thr Tyr Phe Cys
                85                  90                  95

Ser Arg Ser Arg Gly Lys Asn Glu Ala Trp Phe Ala Tyr Trp Gly Gln
            100                 105                 110

Gly Thr Leu Val Thr Val Ser Ser
        115                 120

<210> SEQ ID NO 13
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 13 gac atc cag ctg acc caa act cca ctc tcc ctg cct gtc agt ctt gga      48
Asp Ile Gln Leu Thr Gln Thr Pro Leu Ser Leu Pro Val Ser Leu Gly
1               5                   10                  15 gat caa gcc tcc atc tct tgc aga tct agt cag agc ctt gta cac aga      96
Asp Gln Ala Ser Ile Ser Cys Arg Ser Ser Gln Ser Leu Val His Arg
            20                  25                  30 aat gga aac acc tat tta cat tgg tac ctg cag aag cca ggc cag tct     144
Asn Gly Asn Thr Tyr Leu His Trp Tyr Leu Gln Lys Pro Gly Gln Ser
        35                  40                  45 cca aag ctc ctg atc tac aca gtt tcc aac cga ttt tct ggg gtc cca     192
Pro Lys Leu Leu Ile Tyr Thr Val Ser Asn Arg Phe Ser Gly Val Pro
    50                  55                  60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
65                  70                  75                  80 agt aga gtg gag gct gag gat ctg gga ctt tat ttc tgc tct caa agt     288
Ser Arg Val Glu Ala Glu Asp Leu Gly Leu Tyr Phe Cys Ser Gln Ser
                85                  90                  95 tca cat gtt cct ccc acg ttc ggt gct ggg acc aag ctg gag atc aaa     336
Ser His Val Pro Pro Thr Phe Gly Ala Gly Thr Lys Leu Glu Ile Lys
            100                 105                 110 cgt                                                                 339
Arg

<210> SEQ ID NO 14
<211> LENGTH: 113
<212> TYPE: PRT

<213> ORGANISM: Artificial Sequence
<220> FEATURE:
<223> OTHER INFORMATION: Description of Artificial Sequence: Synthetic
     polypeptide

<400> SEQUENCE: 14

Asp Ile Gln Leu Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Ser His Val Pro Pro Thr Phe Gly Ala Gly Thr Lys Leu Glu Ile Lys
            100                 105                 110

Arg

<210> SEQ ID NO 15
<211> LENGTH: 120
<212> TYPE: PRT
<213> ORGANISM: Homo sapiens

<400> SEQUENCE: 15

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Asp Asp Thr Ala Val Tyr Tyr Cys
                85                  90                  95

Ala Arg Glu Asp Ser Asn Gly Tyr Lys Ile Phe Asp Tyr Trp Gly Gln
            100                 105                 110

Gly Ser Leu Val Thr Val Ser Ser
        115                 120

<210> SEQ ID NO 16
<211> LENGTH: 111
<212> TYPE: PRT
<213> ORGANISM: Homo sapiens

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                     85                  90                  95

Thr His Trp Pro Phe Thr Phe Gly Gln Gly Thr Arg Leu Glu Ile
                100                 105                 110

<210> SEQ ID NO 17
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 17 cag gtc caa ctg cag caa tct ggg tct gag ttg aag aag cct ggg gcc       48
Gln Val Gln Leu Gln Gln Ser Gly Ser Glu Leu Lys Lys Pro Gly Ala
 1               5                  10                  15 tca gtg aag gtt tcc tgc aag gct tct gga tac acc ttc act aac tat       96
Ser Val Lys Val Ser Cys Lys Ala Ser Gly Tyr Thr Phe Thr Asn Tyr
                20                  25                  30 gga gtg aac tgg ata aag cag gcc cct gga caa ggg ctt cag tgg atg      144
Gly Val Asn Trp Ile Lys Gln Ala Pro Gly Gln Gly Leu Gln Trp Met
            35                  40                  45 ggc tgg ata aac ccc aac act gga gag cca aca ttt gat gat gac ttc      192
Gly Trp Ile Asn Pro Asn Thr Gly Glu Pro Thr Phe Asp Asp Asp Phe
        50                  55                  60 aag gga cga ttt gcc ttc tcc ttg gac acc tct gtc agc acg gca tat      240
Lys Gly Arg Phe Ala Phe Ser Leu Asp Thr Ser Val Ser Thr Ala Tyr
 65                  70                  75                  80 ctc cag atc agc agc cta aag gct gac gac act gcc gtg tat ttc tgt      288
Leu Gln Ile Ser Ser Leu Lys Ala Asp Asp Thr Ala Val Tyr Phe Cys
                 85                  90                  95 tca aga tcg agg ggt aaa aac gaa gcc tgg ttt gct tat tgg ggc caa      336
Ser Arg Ser Arg Gly Lys Asn Glu Ala Trp Phe Ala Tyr Trp Gly Gln
            100                 105                 110 ggg agc ctg gtc acc gtc tcc tca                                      360
Gly Ser Leu Val Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
                20                  25                  30

Gly Val Asn Trp Ile Lys Gln Ala Pro Gly Gln Gly Leu Gln Trp Met
            35                  40                  45

Gly Trp Ile Asn Pro Asn Thr Gly Glu Pro Thr Phe Asp Asp Asp Phe
        50                  55                  60
```

-continued

```
Lys Gly Arg Phe Ala Phe Ser Leu Asp Thr Ser Val Ser Thr Ala Tyr
 65                  70                  75                  80

Leu Gln Ile Ser Ser Leu Lys Ala Asp Asp Thr Ala Val Tyr Phe Cys
                 85                  90                  95

Ser Arg Ser Arg Gly Lys Asn Glu Ala Trp Phe Ala Tyr Trp Gly Gln
            100                 105                 110

Gly Ser Leu Val Thr Val Ser Ser
        115                 120

<210> SEQ ID NO 19
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 19 gac atc cag ctg act cag tct cca ctc tcc ctg ccc gtc acc ctt gga      48
Asp Ile Gln Leu Thr Gln Ser Pro Leu Ser Leu Pro Val Thr Leu Gly
 1               5                  10                  15 cag ccg gcc tcc atc tcc tgc aga tca agt cag agc ctt gta cac aga      96
Gln Pro Ala Ser Ile Ser Cys Arg Ser Ser Gln Ser Leu Val His Arg
             20                  25                  30 aat gga aac acc tat tta cat tgg ttt cag cag agg cca ggc caa tct     144
Asn Gly Asn Thr Tyr Leu His Trp Phe Gln Gln Arg Pro Gly Gln Ser
         35                  40                  45 cca agg ctc ctg atc tac aca gtt tcc aac cga ttt tct ggg gtc cca     192
Pro Arg Leu Leu Ile Tyr Thr Val Ser Asn Arg Phe Ser Gly Val Pro
     50                  55                  60 gac aga ttc agc ggc agt ggg tca ggc act gat ttc aca ctg aaa atc     240
Asp Arg Phe Ser Gly Ser Gly Ser Gly Thr Asp Phe Thr Leu Lys Ile
 65                  70                  75                  80 agc agg gtg gag gct gag gat gtt ggg gtt tat ttc tgc tct caa agt     288
Ser Arg Val Glu Ala Glu Asp Val Gly Val Tyr Phe Cys Ser Gln Ser
                 85                  90                  95 tca cat gtt cct ccc acg ttc ggt gct ggg aca cga ctg gag atc aaa     336
Ser His Val Pro Pro Thr Phe Gly Ala Gly Thr Arg Leu Glu Ile Lys
            100                 105                 110 cgt                                                                 339
Arg

<210> SEQ ID NO 20
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Leu Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Arg
             20                  25                  30

Asn Gly Asn Thr Tyr Leu His Trp Phe Gln Gln Arg Pro Gly Gln Ser
         35                  40                  45

Pro Arg Leu Leu Ile Tyr Thr Val Ser Asn Arg Phe Ser Gly Val Pro
     50                  55                  60
```

```
Asp Arg Phe Ser Gly Ser Gly Ser Gly Thr Asp Phe Thr Leu Lys Ile
 65              70              75              80

Ser Arg Val Glu Ala Glu Asp Val Gly Val Tyr Phe Cys Ser Gln Ser
             85              90              95

Ser His Val Pro Pro Thr Phe Gly Ala Gly Thr Arg Leu Glu Ile Lys
            100             105             110

Arg
```

What is claimed is:

1. A method of treating a disease associated with cells that express CD74 comprising
   a. administering to an individual with the disease an immunoconjugate comprising at least one anti-CD74 antibody or antigen-binding fragment thereof attached to a liposome, wherein said administration results in aggregation of CD74 on the surface of CD74-expressing cells; and
   b. inducing apoptosis of the CD74 expressing cells.

2. The method of claim 1, wherein the anti-CD74 antibody or antigen-binding fragment thereof is selected from the group consisting of a monoclonal antibody, an antigen-binding fragment of a monoclonal antibody, a bispecific antibody, a multispecific antibody and an antibody fusion protein.

3. The method of claim 1, wherein the immunoconjugate further comprises at least one therapeutic or diagnostic agent.

4. The method of claim 1, wherein the anti-CD74 antibody is milatuzumab.

5. The method of claim 1, wherein the anti-CD74 antibody comprises the light chain variable region complementarity-determining region (CDR) sequences CDR1 (RSSQS-LVHRNGNTYLH; SEQ ID NO:1), CDR2 (TVSNRFS; SEQ ID NO:2), and CDR3 (SQSSHVPPT; SEQ ID NO:3) and the heavy chain variable region CDR sequences CDR1 (NYGVN; SEQ ID NO:4), CDR2 (WINPNTGEPTFD-DDFKG; SEQ ID NO:5), and CDR3 (SRGKNEAWFAY; SEQ ID NO:6).

6. The method of claim 1, wherein the anti-CD74 antibody is a chimeric, humanized or human antibody.

7. The method of claim 1, wherein the anti-CD74 antibody or fragment thereof is a naked anti-CD74 antibody or fragment thereof.

8. The method of claim 7, further comprising administering at least one therapeutic agent to said individual before, simultaneously with or after the immunoconjugate.

9. The method of claim 1, wherein the anti-CD74 antibody or fragment thereof is conjugated to at least one therapeutic or diagnostic agent.

10. The method of claim 1, wherein the at least one anti-CD74 antibody or antigen-binding fragment thereof is conjugated to the liposome by a linkage selected from the group consisting of a sulfide linkage, a hydrazone linkage, a hydrazine linkage, an ester linkage, an amido linkage, an amino linkage, an imino linkage, a thiosemicarbazone linkage, a semicarbazone linkage, an oxime linkage, a carbon-carbon linkage, or a combination thereof.

11. The method of claim 3, wherein the therapeutic or diagnostic agent is selected from the group consisting of a drug, a prodrug, a toxin, an enzyme, a radionuclide, an immunomodulator, a cytokine, a hormone, a second antibody or antigen-binding fragment thereof, an antisense oligonucleotide, an RNAi, an anti-angiogenic agent, a pro-apoptosis agent, a dye, a fluorescent agent, a contrast agent, a paramagnetic ion and a photodynamic agent.

12. The method of claim 1, wherein immunoconjugate further comprises a second antibody or antigen-binding fragment thereof that binds to an antigen selected from the group consisting of carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM-6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IL-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, PAM4 antigen, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5, and an oncogene product.

13. The method of claim 11, wherein the therapeutic agent is selected from the group consisting of aplidin, azaribine, anastrozole, azacytidine, bleomycin, bortezomib, bryostatin-1, busulfan, calicheamicin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, Pseudomonas exotoxin, and Pseudomonas endotoxin.

14. The method of claim 13, wherein the therapeutic agent comprises FUdR, FUdR-dO, or mixtures thereof.

15. The method of claim 1, wherein the immunoconjugate further comprises one or more hard acid chelators or soft acid chelators.

16. The method of claim 15, wherein the immunoconjugate further comprises one or more cations selected from Group II, Group III, Group IV, Group V, transition, lanthanide or actinide metal cations, or mixtures thereof, wherein said cation is attached to the one or more hard or soft acid chelators.

17. The method of claim 16, wherein the cation is selected from the group consisting of Tc, Re, Bi, Cu, As, Ag, Au, At and Pb.

18. The method of claim 15, wherein said chelator is selected from the group consisting of NOTA, DOTA, DTPA, TETA, Tscg-Cys and Tsca-Cys.

19. The method of claim 11, wherein the radionuclide is selected from the group consisting of $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{75}Se$, $^{77}As$, $^{86}Y$, $^{89}Sr$, $^{89}Zr$, $^{90}Y$, $^{94}TC$, $^{94m}TC$, $^{99}Mo$, $^{99m}Tc$, $^{105}Pd$, $^{105}Rb$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154\text{-}158}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$ and $^{225}Ac$.

20. The method of claim 11, wherein the enzyme is selected from the group consisting of carboxylesterase, glucuronidase, carboxypeptidase, beta-lactamase and phosphatase.

21. The method of claim 11, wherein the immunomodulator is selected from the group consisting of a cytokine, a stem cell growth factor, a lymphotoxin, a hematopoietic factor, a colony stimulating factor (CSF), an interleukin (IL) and an interferon (IFN).

22. The method of claim 21, wherein the immunomodulator is selected from the group consisting of erythropoietin, thrombopoietin tumor necrosis factor-α (TNF), TNF-β, granulocyte-colony stimulating factor (G-CSF), granulocyte macrophage-colony stimulating factor (GM-CSF), interferon-α, interferon-β, interferon-γ, stem cell growth factor designated "S1 factor", human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, mullerian-inhibiting substance, mouse gonadotropin-associated peptide, inhibin, activin, vascular endothelial growth factor, integrin, NGF-β, platelet-growth factor, TGF-α, TGF-β, insulin-like growth factor-I, insulin-like growth factor-II, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, and endostatin.

23. The method of claim 11, wherein the anti-angiogenic agent is selected from the group consisting of angiostatin, endostatin, baculostatin, canstatin, maspin, anti-VEGF binding molecules, anti-placental growth factor binding molecules and anti-vascular growth factor binding molecules.

24. The method of claim 1, wherein the antibody fragment is selected from the group consisting of F(ab')$_2$, F(ab)$_2$, Fab, Fab' and scFv fragments.

25. The method of claim 6, wherein the human, chimeric, or humanized anti-CD74 antibody or fragment thereof further comprises human constant regions selected from the group consisting of IgG1, IgG2a, IgG3 and IgG4.

26. The method of claim 1, wherein the disease is selected from the group consisting of an immune dysregulation disease, an autoimmune disease, an organ-graft rejection, a graft-versus-host disease and cancer.

27. The method of claim 26, wherein the cancer is selected from the group consisting of a solid tumor, leukemia, lymphoma, non-Hodgkin's lymphoma, Hodgkin's lymphoma, multiple myeloma, a B-cell malignancy and a T-cell malignancy.

28. The method of claim 27, wherein the solid tumor is selected from the group consisting of a melanoma, carcinoma, sarcoma, and glioma.

29. The method of claim 28, wherein the carcinoma is selected from the group consisting of a renal carcinoma, lung carcinoma, intestinal carcinoma, stomach carcinoma, breast carcinoma, prostate cancer and ovarian cancer.

30. The method of claim 27, wherein the B-cell malignancy is selected from the group consisting of indolent forms of B-cell lymphomas, aggressive forms of B-cell lymphomas, chronic lymphocytic leukemias, acute lymphocytic leukemias and multiple myeloma.

31. The method of claim 11, wherein the photodynamic agent is selected from the group consisting of benzoporphyrin monoacid ring A (BDP-MA), tin etiopurpurin (SnET2), sulfonated aluminum phthalocyanine (AISPc) and lutetium texaphyrin (Lutex).

32. The method of claim 11, wherein the diagnostic agent is a radionuclide selected from the group consisting of $^{18}F$, $^{52}Fe$, $^{62}Cu$, $^{64}Cu$, $^{67}Cu$, $^{67}Ga$, $^{68}Ga$, $^{86}Y$, $^{89}Zr$, $^{94}Tc$, $^{94m}Tc$, $^{99m}Tc$, $^{111}In$, $^{123}I$, $^{124}I$, $^{125}I$ and $^{131}I$.

33. The method of claim 11, wherein the diagnostic agent is a contrast agent selected from the group consisting of gadolinium ions, lanthanum ions, manganese ions, iron, chromium, copper, cobalt, nickel, fluorine, dysprosium, rhenium, europium, terbium, holmium, neodymium, barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone and thallous chloride.

34. The method of claim 1, wherein the immunoconjugate is administered by intravenous, intramuscular, intraperitoneal, intravascular, parenteral or subcutaneous administration.

* * * * *